US010376195B1

(12) United States Patent
Reid et al.

(10) Patent No.: US 10,376,195 B1
(45) Date of Patent: Aug. 13, 2019

(54) AUTOMATED NURSING ASSESSMENT

(71) Applicant: Google, Inc., Mountain View, CA (US)

(72) Inventors: James M. Reid, Mountain View, CA (US); Jeffrey L. Rogers, San Carlos, CA (US); Brian Derek DeBusschere, Los Gatos, CA (US)

(73) Assignee: Google LLC, Mountain View, CA (US)

( * ) Notice: Subject to any disclaimer, the term of this patent is extended or adjusted under 35 U.S.C. 154(b) by 809 days.

(21) Appl. No.: 14/731,195

(22) Filed: Jun. 4, 2015

(51) Int. Cl.
*A61B 5/0205* (2006.01)
*A61B 5/16* (2006.01)
(Continued)

(52) U.S. Cl.
CPC ............... *A61B 5/165* (2013.01); *A61B 3/02* (2013.01); *A61B 5/0077* (2013.01); *A61B 5/01* (2013.01);
(Continued)

(58) Field of Classification Search
USPC ........................................................ 434/236
See application file for complete search history.

(56) References Cited

U.S. PATENT DOCUMENTS 5,121,124 A 6/1992 Spivey et al.
5,410,471 A 4/1995 Alyfuku et al.
(Continued)

FOREIGN PATENT DOCUMENTS

CN 102660988 3/2014
EP 2417908 2/2012
(Continued)

OTHER PUBLICATIONS

"Final Office Action", U.S. Appl. No. 14/518,863, dated May 5, 2017, 18 pages.
(Continued)

*Primary Examiner* — Kesha Frisby
(74) *Attorney, Agent, or Firm* — Colby Nipper PLLC

(57) ABSTRACT

This document describes automated nursing assessments. Automation of the nursing assessment involves a nursing-assessment device that makes determinations of a person's mood, physical state, psychosocial state, and neurological state. To determine a mood and physical state of a person, video of the person is captured while the person is positioned in front of an everyday object, such as a mirror. The captured video is then processed according to human condition recognition techniques, which produces indications of the person's mood and physical state, such as whether the person is happy, sad, healthy, sick, vital signs, and so on. In addition to mood and physical state, the person's psychosocial and neurological state are also determined. To do so, questions are asked of the person. These questions are determined from a plurality of psychosocial and neurological state assessment questions, which include queries regarding how the person feels, what the person has been doing, and so on. The determined questions are asked through audible or visual interfaces of the nursing-assessment device. The person's responses are then analyzed. The analysis involves processing the received answers according to psychosocial and neurological state assessment techniques to produce indications of the person's psychosocial and neurological state.

20 Claims, 7 Drawing Sheets

(51) Int. Cl.
*A61B 5/01* (2006.01)
*A61B 5/021* (2006.01)
*A61B 5/08* (2006.01)
*A61B 5/024* (2006.01)
*A61B 5/11* (2006.01)
*A61B 3/02* (2006.01)
*G09B 19/00* (2006.01)
*A61B 5/00* (2006.01)

(52) U.S. Cl.
CPC .............. *A61B 5/021* (2013.01); *A61B 5/024* (2013.01); *A61B 5/0205* (2013.01); *A61B 5/08* (2013.01); *A61B 5/1123* (2013.01); *A61B 5/1124* (2013.01); *A61B 5/7405* (2013.01); *A61B 5/7445* (2013.01); *G09B 19/00* (2013.01)

(56) References Cited

U.S. PATENT DOCUMENTS

| | | |
|---|---|---|
| 5,798,798 A | 8/1998 | Rector et al. |
| 6,254,544 B1 | 7/2001 | Hayashi |
| 6,313,825 B1 | 11/2001 | Gilbert |
| 6,386,757 B1 | 5/2002 | Konno |
| 6,513,970 B1 | 2/2003 | Tabata et al. |
| 6,524,239 B1 | 2/2003 | Reed et al. |
| 6,616,613 B1 | 9/2003 | Goodman |
| 6,997,882 B1 | 2/2006 | Parker et al. |
| 7,194,371 B1 | 3/2007 | McBride et al. |
| 7,317,416 B2 | 1/2008 | Flom et al. |
| 7,421,061 B2 | 9/2008 | Boese et al. |
| 7,647,093 B2 | 1/2010 | Bojovic et al. |
| 7,677,729 B2 | 3/2010 | Vilser et al. |
| 7,691,067 B2 | 4/2010 | Westbrook et al. |
| 7,698,154 B2 | 4/2010 | Marchosky |
| 8,062,220 B2 | 11/2011 | Kurtz et al. |
| 8,179,604 B1 | 5/2012 | Prada Gomez et al. |
| 8,193,929 B1 | 6/2012 | Siu et al. |
| 8,289,185 B2 | 10/2012 | Alonso |
| 8,301,232 B2 | 10/2012 | Albert et al. |
| 8,475,367 B1 | 7/2013 | Yuen et al. |
| 8,509,882 B2 | 8/2013 | Albert et al. |
| 8,560,972 B2 | 10/2013 | Wilson |
| 8,562,526 B2 | 10/2013 | Heneghan et al. |
| 8,655,004 B2 | 2/2014 | Prest et al. |
| 8,700,137 B2 | 4/2014 | Albert |
| 8,758,020 B2 | 6/2014 | Burdea et al. |
| 8,764,651 B2 | 7/2014 | Tran |
| 8,790,257 B2 | 7/2014 | Libbus et al. |
| 8,819,812 B1 | 8/2014 | Weber et al. |
| 9,230,160 B1 | 1/2016 | Kanter |
| 9,508,141 B2 | 11/2016 | Khachaturian et al. |
| 9,594,443 B2 | 3/2017 | Vanblon et al. |
| 9,600,080 B2 | 3/2017 | Poupyrev |
| 9,778,749 B2 | 10/2017 | Poupyrev |
| 9,811,164 B2 | 11/2017 | Poupyrev |
| 9,848,780 B1 | 12/2017 | Debusschere et al. |
| 9,921,660 B2 | 3/2018 | Poupyrev |
| 10,016,162 B1 | 7/2018 | Rogers et al. |
| 10,064,582 B2 | 9/2018 | Rogers |
| 10,080,528 B2 | 9/2018 | Debusschere et al. |
| 2003/0093000 A1 | 5/2003 | Nishio et al. |
| 2003/0122677 A1 | 7/2003 | Kail |
| 2004/0102693 A1 | 5/2004 | Jenkins |
| 2004/0249250 A1 | 12/2004 | McGee et al. |
| 2005/0148876 A1 | 7/2005 | Endoh et al. |
| 2006/0040739 A1 | 2/2006 | Wells |
| 2007/0118043 A1 | 5/2007 | Oliver et al. |
| 2007/0161921 A1 | 7/2007 | Rausch |
| 2007/0176821 A1 | 8/2007 | Flom et al. |
| 2007/0197878 A1 | 8/2007 | Shklarski |
| 2008/0001735 A1 | 1/2008 | Tran |
| 2008/0015422 A1 | 1/2008 | Wessel |
| 2008/0039731 A1 | 2/2008 | McCombie et al. |
| 2008/0065291 A1 | 3/2008 | Breed |
| 2008/0168396 A1 | 7/2008 | Matas et al. |
| 2008/0194975 A1 | 8/2008 | MacQuarrie et al. |
| 2008/0211766 A1 | 9/2008 | Westerman et al. |
| 2008/0316085 A1 | 12/2008 | Rofougaran et al. |
| 2008/0320419 A1 | 12/2008 | Matas et al. |
| 2009/0018408 A1 | 1/2009 | Ouchi et al. |
| 2009/0058820 A1 | 3/2009 | Hinckley |
| 2009/0113298 A1 | 4/2009 | Jung et al. |
| 2009/0115617 A1 | 5/2009 | Sano et al. |
| 2009/0177068 A1 | 7/2009 | Stivoric et al. |
| 2009/0253585 A1* | 10/2009 | Diatchenko .......... C12Q 1/6883 506/9 |
| 2009/0270690 A1 | 10/2009 | Roos et al. |
| 2009/0295712 A1 | 12/2009 | Ritzau |
| 2009/0319181 A1 | 12/2009 | Khosravy et al. |
| 2010/0069730 A1 | 3/2010 | Bergstrom et al. |
| 2010/0094141 A1 | 4/2010 | Puswella |
| 2010/0179820 A1 | 7/2010 | Harrison et al. |
| 2010/0204550 A1 | 8/2010 | Heneghan et al. |
| 2010/0281438 A1 | 11/2010 | Latta et al. |
| 2010/0292549 A1 | 11/2010 | Schuler |
| 2010/0306713 A1 | 12/2010 | Geisner et al. |
| 2010/0324384 A1 | 12/2010 | Moon et al. |
| 2011/0003664 A1 | 1/2011 | Richard |
| 2011/0010014 A1 | 1/2011 | Oexman et al. |
| 2011/0029038 A1 | 2/2011 | Hyde et al. |
| 2011/0093820 A1 | 4/2011 | Zhang et al. |
| 2011/0118564 A1 | 5/2011 | Sankai |
| 2011/0181509 A1 | 7/2011 | Rautiainen et al. |
| 2011/0197263 A1 | 8/2011 | Stinson, III |
| 2011/0202404 A1 | 8/2011 | van der Riet |
| 2011/0213218 A1 | 9/2011 | Weiner et al. |
| 2011/0221666 A1 | 9/2011 | Newton et al. |
| 2011/0234492 A1 | 9/2011 | Ajmera et al. |
| 2011/0239118 A1 | 9/2011 | Yamaoka et al. |
| 2011/0245688 A1 | 10/2011 | Arora et al. |
| 2011/0307842 A1 | 12/2011 | Chiang et al. |
| 2012/0019168 A1 | 1/2012 | Noda et al. |
| 2012/0029369 A1 | 2/2012 | Icove et al. |
| 2012/0047468 A1 | 2/2012 | Santos et al. |
| 2012/0123232 A1 | 5/2012 | Najarian et al. |
| 2012/0174736 A1 | 7/2012 | Wang et al. |
| 2012/0220835 A1 | 8/2012 | Chung |
| 2012/0254810 A1 | 10/2012 | Heck et al. |
| 2012/0280900 A1 | 11/2012 | Wang et al. |
| 2012/0310665 A1 | 12/2012 | Xu et al. |
| 2013/0035563 A1 | 2/2013 | Angellides |
| 2013/0053653 A1 | 2/2013 | Cuddihy et al. |
| 2013/0083173 A1 | 4/2013 | Geisner et al. |
| 2013/0096439 A1 | 4/2013 | Lee et al. |
| 2013/0132931 A1 | 5/2013 | Bruns et al. |
| 2013/0150735 A1 | 6/2013 | Cheng |
| 2013/0195330 A1 | 8/2013 | Kim et al. |
| 2013/0278499 A1 | 10/2013 | Anderson |
| 2013/0278501 A1 | 10/2013 | Bulzacki |
| 2013/0283203 A1 | 10/2013 | Batraski et al. |
| 2013/0322729 A1 | 12/2013 | Mestha et al. |
| 2013/0332438 A1 | 12/2013 | Li et al. |
| 2013/0345569 A1 | 12/2013 | Mestha et al. |
| 2014/0005809 A1 | 1/2014 | Frei et al. |
| 2014/0051941 A1 | 2/2014 | Messerschmidt |
| 2014/0072190 A1 | 3/2014 | Wu et al. |
| 2014/0073486 A1 | 3/2014 | Ahmed et al. |
| 2014/0073969 A1 | 3/2014 | Zou et al. |
| 2014/0081100 A1 | 3/2014 | Muhsin et al. |
| 2014/0095480 A1 | 4/2014 | Marantz et al. |
| 2014/0121540 A1 | 5/2014 | Raskin |
| 2014/0135631 A1 | 5/2014 | Brumback et al. |
| 2014/0139616 A1 | 5/2014 | Pinter et al. |
| 2014/0143678 A1 | 5/2014 | Mistry et al. |
| 2014/0191939 A1 | 7/2014 | Penn et al. |
| 2014/0200416 A1 | 7/2014 | Kashef et al. |
| 2014/0244277 A1 | 8/2014 | Krishna Rao et al. |
| 2014/0250515 A1 | 9/2014 | Jakobsson |
| 2014/0253709 A1 | 9/2014 | Bresch et al. |
| 2014/0275854 A1 | 9/2014 | Venkatraman et al. |
| 2014/0280295 A1 | 9/2014 | Kurochikin et al. |
| 2014/0297006 A1 | 10/2014 | Sadhu |

(56) References Cited

U.S. PATENT DOCUMENTS

| | | |
|---|---|---|
| 2014/0306936 A1 | 10/2014 | Dahl et al. |
| 2014/0316261 A1 | 10/2014 | Lux et al. |
| 2014/0357369 A1 | 12/2014 | Callens et al. |
| 2014/0376788 A1 | 12/2014 | Xu et al. |
| 2015/0026815 A1 | 1/2015 | Barrett |
| 2015/0029050 A1 | 1/2015 | Driscoll et al. |
| 2015/0046183 A1 | 2/2015 | Cireddu |
| 2015/0077282 A1 | 3/2015 | Mohamadi |
| 2015/0085060 A1 | 3/2015 | Fish et al. |
| 2015/0095987 A1 | 4/2015 | Potash et al. |
| 2015/0099941 A1 | 4/2015 | Tran |
| 2015/0100328 A1 | 4/2015 | Kress et al. |
| 2015/0112606 A1 | 4/2015 | He et al. |
| 2015/0277569 A1 | 10/2015 | Sprenger et al. |
| 2015/0287187 A1 | 10/2015 | Redtel |
| 2015/0312041 A1 | 10/2015 | Choi |
| 2015/0346820 A1 | 12/2015 | Poupyrev et al. |
| 2015/0351703 A1 | 12/2015 | Phillips et al. |
| 2016/0041617 A1 | 2/2016 | Poupyrev |
| 2016/0041618 A1 | 2/2016 | Poupyrev |
| 2016/0054792 A1 | 2/2016 | Poupyrev |
| 2016/0054803 A1 | 2/2016 | Poupyrev |
| 2016/0054804 A1 | 2/2016 | Gollakata et al. |
| 2016/0055201 A1 | 2/2016 | Poupyrev et al. |
| 2016/0098089 A1 | 4/2016 | Poupyrev |
| 2016/0100166 A1 | 4/2016 | Dragne et al. |
| 2016/0106328 A1 | 4/2016 | Mestha et al. |
| 2016/0206244 A1 | 7/2016 | Rogers |
| 2016/0213331 A1 | 7/2016 | Gil et al. |
| 2016/0220152 A1 | 8/2016 | Meriheina et al. |
| 2016/0287172 A1 | 10/2016 | Morris et al. |
| 2016/0321428 A1 | 11/2016 | Rogers |
| 2016/0338599 A1 | 11/2016 | DeBusschere et al. |
| 2017/0192523 A1 | 7/2017 | Poupyrev |
| 2018/0000354 A1 | 1/2018 | Debusschere et al. |
| 2018/0000355 A1 | 1/2018 | Debusschere et al. |
| 2018/0004301 A1 | 1/2018 | Poupyrev |
| 2018/0046258 A1 | 2/2018 | Poupyrev |
| 2018/0177464 A1 | 6/2018 | Debusschere et al. |
| 2018/0256106 A1 | 9/2018 | Rogers et al. |
| 2018/0296163 A1 | 10/2018 | Debusschere et al. |

FOREIGN PATENT DOCUMENTS

| | | |
|---|---|---|
| FR | 3017722 | 8/2015 |
| JP | 113860 | 4/1999 |
| WO | WO-9001895 | 3/1990 |
| WO | WO-2001027855 | 4/2001 |
| WO | WO-2002082999 | 10/2002 |
| WO | 2004004557 | 1/2004 |
| WO | WO-2009032073 | 3/2009 |
| WO | WO-2013186696 | 12/2013 |
| WO | WO-2013191657 | 12/2013 |
| WO | WO-2013192166 | 12/2013 |
| WO | WO-2014116968 | 7/2014 |
| WO | WO-2014124520 | 8/2014 |
| WO | WO-2014136027 | 9/2014 |
| WO | WO-2014138280 | 9/2014 |
| WO | WO-2014160893 | 10/2014 |
| WO | 2016118534 | 7/2016 |
| WO | 2016176471 | 11/2016 |
| WO | 2016178797 | 11/2016 |
| WO | 2017019299 | 2/2017 |

OTHER PUBLICATIONS

"International Preliminary Report on Patentability", Application No. PCT/US2015/050903, dated Apr. 13, 2017, 12 pages.

"Notice of Allowance", U.S. Appl. No. 14/599,954, May 24, 2017, 11 pages.

"Notice of Allowance", U.S. Appl. No. 14/494,863, dated May 30, 2017, 7 pages.

"Notice of Allowance", U.S. Appl. No. 14/681,625, dated Jun. 7, 2017, 7 pages.

"Apple Watch Used Four Sensors to Detect your Pulse", retrieved from http://www.theverge.com/2014/9/9/6126991 /apple-watch-four-back-sensors-detect-activity on Sep. 23, 2017 as cited in PCT search report for PCT Application No. PCT/US2016/026756 dated Nov. 10, 2017; The Verge, paragraph 1, Sep. 9, 2014, 4 pages.

"Non-Invasive Quantification of Peripheral Arterial Volume Distensibilitiy and its Non-Lineaer Relationship with Arterial Pressure", Journal of Biomechanics, Pergamon Press, vol. 42, No. 8; as cited in the search report for PCT/US2016/013968 citing the whole document, but in particular the abstract, dated May 29, 2009, 2 pages.

"Pressure-Volume Loop Analysis in Cardiology", retrieved from https://en.wikipedia.org/w/index.php?t itle=Pressure-volume loop analysis in card iology&oldid=636928657 on Sep. 23, 2017; Obtained per link provided in search report from PCT/US2016/01398 dated Jul. 28, 2016, Dec. 6, 2014, 10 pages.

"Written Opinion", PCT Application No. PCT/US2016/042013, dated Feb. 2, 2017, 6 pages.

"Written Opinion", PCT Application PCT/US2016/013968, dated Jul. 28, 2016, 9 pages.

"Written Opinion", PCT Application No. PCT/US2016/026756, dated Nov. 10, 2016, 7 pages.

Ishijima, "Unobtrusive Approaches to Monitoring Vital Signs at Home", Medical & Biological Engineering and Computing, Springer, Berlin, DE, vol. 45, No. 11 as cited in search report for PCT/US2016/013968 dated Jul. 28, 2016, Sep. 26, 2007, 3 pages.

"Clever Toilet Checks on Your Health", CNN.Com; Technology, Jun. 28, 2005, 2 pages.

"Final Office Action", U.S. Appl. No. 14/504,121, dated Aug. 8, 2017, 16 pages.

"Final Office Action", U.S. Appl. No. 14/715,454, dated Sep. 7, 2017, 14 pages.

"Final Office Action", U.S. Appl. No. 14/715,793, dated Sep. 12, 2017, 7 pages.

"First Action Interview OA", U.S. Appl. No. 14/715,793, dated Jun. 21, 2017, 3 pages.

"Non-Final Office Action", U.S. Appl. No. 14/720,632, dated Jun. 12, 2017, 16 pages.

"Notice of Allowance", U.S. Appl. No. 14/513,875, dated Jun. 28, 2017, 7 pages.

"Notice of Allowance", U.S. Appl. No. 14/666,155, dated Jul. 10, 2017, 7 pages.

"Notice of Allowance", U.S. Appl. No. 14/504,038, dated Aug. 7, 2017, 17 pages.

Otto, et al., "System Architecture of a Wireless Body Area Sensor Network for Ubiquitous Health Monitoring", Journal of Mobile Multimedia; vol. 1, No. 4, Jan. 10, 2006, 20 pages.

"Final Office Action", U.S. Appl. No. 14/720,632, dated Jan. 9, 2018, 18 pages.

"Non-Final Office Action", U.S. Appl. No. 14/715,454, dated Jan. 11, 2018, 16 pages.

"Non-Final Office Action", U.S. Appl. No. 14/504,121, dated Jan. 2, 2018, 19 pages.

"Notice of Allowance", U.S. Appl. No. 14/666,155, dated Feb. 20, 2018, 5 pages.

"Notice of Allowance", U.S. Appl. No. 14/599,954, dated Mar. 15, 2018, 9 pages.

"Preliminary Report on Patentability", PCT Application No. PCT/US2016/042013, dated Jan. 30, 2018, 7 pages.

"Thermofocus No Touch Forehead Thermometer", Technimed, Internet Archive. Dec. 24, 2014. https://web.archive.org/web/20141224070848/http://www.tecnimed.it:80/thermofocus-forehead-thermometer-H1N1-swine-flu.html, Dec. 24, 2018, 4 pages.

"International Preliminary Report on Patentability", PCT Application No. PCT/US2016/026756, dated Oct. 19, 2017, 8 pages.

"Non-Final Office Action", U.S. Appl. No. 14/518,863, dated Sep. 29, 2017, 20 pages.

"Non-Final Office Action", U.S. Appl. No. 14/699,181, dated Oct. 18, 2017, 33 pages.

"Notice of Allowance", U.S. Appl. No. 14/681,625, dated Oct. 23, 2017, 8 pages.

"Notice of Allowance", U.S. Appl. No. 14/715,793, dated Dec. 18, 2017, 5 pages.

(56) References Cited

OTHER PUBLICATIONS

"Preliminary Report on Patentability", PCT Application No. PCT/US20161032307, dated Dec. 7, 2017, 9 pages.
"Final Office Action", U.S. Appl. No. 14/715,454, dated Apr. 17, 2018, 19 pages.
"Final Office Action", U.S. Appl. No. 14/518,863, dated Apr. 5, 2018, 21 pages.
"Final Office Action", U.S. Appl. No. 14/699,181, dated May 4, 2018, 41 pages.
"Final Office Action", U.S. Appl. No. 14/504,121, dated Jul. 9, 2018, 23 pages.
"Non-Final Office Action", U.S. Appl. No. 14/720,632, dated May 18, 2018, 20 pages.
"Non-Final Office Action", U.S. Appl. No. 14/809,901, dated May 24, 2018, 13 pages.
"Notice of Allowance", U.S. Appl. No. 14/715,793, dated Jul. 6, 2018, 5 pages.
"Final Office Action", U.S. Appl. No. 14/809,901, dated Dec. 13, 2018, 7 pages.
"Pre-Interview Communication", U.S. Appl. No. 15/703,511, dated Feb. 11, 2019, 5 pages.
"Restriction Requirement", U.S. Appl. No. 15/462,957, dated Jan. 4, 2019, 6 pages.
"Corrected Notice of Allowance", U.S. Appl. No. 14/582,896, dated Feb. 6, 2017, 2 pages.
"Corrected Notice of Allowance", U.S. Appl. No. 14/582,896, dated Feb. 23, 2017, 2 pages.
"International Preliminary Report on Patentability", Application No. PCT/US2015/043963, dated Feb. 16, 2017, 12 pages.
"International Preliminary Report on Patentability", Application No. PCT/US2015/043949, dated Feb. 16, 2017, 13 pages.
"Life:X Lifestyle eXplorer", Retrieved from <https://web.archive.org/web/20150318093841/http://research.microsoft.com/en-us/projects/lifex >, Feb. 3, 2017, 2 pages.
"Non-Final Office Action", U.S. Appl. No. 14/504,038, dated Mar. 22, 2017, 33 pages.
"Non-Final Office Action", U.S. Appl. No. 14/513,875, dated Feb. 21, 2017, 9 pages.
"Non-Final Office Action", U.S. Appl. No. 14/599,954, dated Jan. 26, 2017, 16 pages.
"Non-Final Office Action", U.S. Appl. No. 14/666,155, dated Feb. 3, 2017, 12 pages.
"Non-Final Office Action", U.S. Appl. No. 14/681,625, dated Mar. 6, 2017, 7 pages.
"Pre-Interview Communication", U.S. Appl. No. 14/494,863, dated Jan. 27, 2017, 5 pages.
"Pre-Interview Communication", U.S. Appl. No. 14/715,454, dated Apr. 14, 2017, 3 pages.
"Pre-Interview Communication", U.S. Appl. No. 14/715,793, dated Mar. 20, 2017, 3 pages.
"The Dash smart earbuds play back music, and monitor your workout", Retrieved from <http://newatlas.com/bragi-dash-tracking-earbuds/30808/>, Feb. 13, 2014, 3 pages.
Palese,"The Effects of Earphones and Music on the Temperature Measured by Infrared Tympanic Thermometer: Preliminary Results", ORL—head and neck nursing: official journal of the Society of Otorhinolaryngology and Head-Neck Nurses 32.2, 2013, pp. 8-12.
"Cardiio", Retrieved From: <http://www.cardiio.com/> Apr. 15, 2015 App Information Retrieved From: <https://itunes.apple.com/us/app/cardiio-touchless-camera-pulse/id542891434?Is=1&mt=8> Apr. 15, 2015, Feb. 24, 2015, 6 pages.
"Philips Vital Signs Camera", Retrieved From: <http://www.vitalsignscamera.com/> Apr. 15, 2015, Jul. 17, 2013, 2 pages.
Balakrishnan,"Detecting Pulse from Head Motions in Video", In Proceedings: CVPR '13 Proceedings of the 2013 IEEE Conference on Computer Vision and Pattern Recognition Available at: <http://people.csail.mit.edu/mrub/vidmag/papers/Balakrishnan_Detecting_Pulse_from_2013_CVPR_paper.pdf>, Jun. 23, 2013, 8 pages.
Couderc,"Detection of Atrial Fibrillation using Contactless Facial Video Monitoring", In Proceedings: Heart Rhythm Society, vol. 12, Issue 1 Available at: <http://www.heartrhythmjournal.com/article/S1547-5271(14)00924-2/pdf>, Jan. 2015, 7 pages.
He,"A Continuous, Wearable, and Wireless Heart Monitor Using Head Ballistocardiogram (BCG) and Head Electrocardiogram (ECG) with a Nanowatt ECG Heartbeat Detection Circuit", In Proceedings: Thesis, Department of Electrical Engineering and Computer Science, Massachusetts Institute of Technology Available at: <http://dspace.mit.edu/handle/1721.1/79221>, Feb. 2013, 137 pages.
Nakajima,"Development of Real-Time Image Sequence Analysis for Evaluating Posture Change and Respiratory Rate of a Subject in Bed", In Proceedings: Physiological Measurement, vol. 22, No. 3 Retrieved From: <http://iopscience.iop.org/0967-3334/22/3/401/pdf/0967-3334_22_3_401.pdf> Feb. 27, 2015, Aug. 2001, 8 pages.
Poh,"A Medical Mirror for Non-contact Health Monitoring", In Proceedings: ACM SIGGRAPH Emerging Technologies Available at: <http://affect.media.mit.edu/pdfs/11.Poh-etal-SIGGRAPH.pdf>, 2011, 1 page.
Poh,"Non-contact, Automated Cardiac Pulse Measurements Using Video Imaging and Blind Source Separation.", In Proceedings: Optics Express, vol. 18, No. 10 Available at: <http://www.opticsinfobase.org/view_article.cfm?gotourl=http%3A%2F%2Fwww%2Eopticsinfobase%2Eorg%2FDirectPDFAccess%2F771304D55%2DBC95%2D6937%2D5BAC49A426378C02%5F199381%2Foe%2D18%2D10%2D10762%2Ep, May 7, 2010, 13 pages.
Wang,"Exploiting Spatial Redundancy of Image Sensor for Motion Robust rPPG", In Proceedings: IEEE Transactions on Biomedical Engineering, vol. 62, Issue 2, Jan. 19, 2015, 11 pages.
"Final Office Action", U.S. Appl. No. 14/599,954, dated Aug. 10, 2016, 23 pages.
"International Search Report and Written Opinion", U.S. Appl. No. PCT/US2016/029820, dated Jul. 15, 2016, 14 pages.
"Non-Final Office Action", U.S. Appl. No. 14/582,896, dated Jun. 29, 2016, 9 pages.
"Non-Final Office Action", U.S. Appl. No. 14/681,625, dated Aug. 12, 2016, 9 pages.
"Restriction Requirement", U.S. Appl. No. 14/666,155, dated Jul. 22, 2016, 5 pages.
"The Instant Blood Pressure app estimates blood pressure with your smartphone and our algorithm", Retrieved at: http://www.instantbloodpressure.com/—on Jun. 23, 2016, 6 pages.
Klabunde,"Ventricular Pressure-Volume Loop Changes in Valve Disease", Retrieved From <https://web.archive.org/web/20101201185256/http://cvphysiology.com/Heart%20Disease/HD009.htm>, Dec. 1, 2010, 8 pages.
"Final Office Action", U.S. Appl. No. 14/504,038, dated Sep. 27, 2016, 23 pages.
"International Search Report and Written Opinion", Application No. PCT/US2016/032307, dated Aug. 25, 2016, 13 pages.
"Non-Final Office Action", U.S. Appl. No. 14/518,863, dated Oct. 14, 2016, 16 pages.
"Non-Final Office Action", U.S. Appl. No. 14/666,155, dated Aug. 24, 2016, 9 pages.
"Pre-Interview Communication", U.S. Appl. No. 14/513,875, dated Oct. 21, 2016, 3 pages.
Espina,"Wireless Body Sensor Network for Continuous Cuff-less Blood Pressure Monitoring", International Summer School on Medical Devices and Biosensors, 2006, Sep. 2006, 5 pages.
"Non-Final Office Action", U.S. Appl. No. 14/599,954, dated Feb. 2, 2016, 17 pages.
"Non-Final Office Action", U.S. Appl. No. 14/504,038, dated Feb. 26, 2016, 22 pages.
"Corrected Notice of Allowance", U.S. Appl. No. 14/582,896, dated Dec. 19, 2016, 2 pages.
"Final Office Action", U.S. Appl. No. 14/681,625, dated Dec. 7, 2016, 10 pages.
"International Search Report and Written Opinion", Application No. PCT/US2016/042013, dated Oct. 26, 2016, 12 pages.
"International Search Report and Written Opinion", Application No. PCT/US2016/033342, dated Oct. 27, 2016, 20 pages.
"Non-Final Office Action", U.S. Appl. No. 14/504,121, dated Jan. 9, 2017, 13 pages.
"Notice of Allowance", U.S. Appl. No. 14/582,896, dated Nov. 7, 2016, 5 pages.

(56) References Cited

OTHER PUBLICATIONS

Matthews,"Venous Pulse", Retrieved at http://www.rjmatthewsmd.com/Definitions/venous_pulse.htm—on Nov. 30, 2016, Apr. 13, 2013, 7 pages.

"Non-Final Office Action", Application No. 15/462,957, dated May 24, 2019, 14 pages.

"Notice of Allowance", Application No. 15/703,511, Apr. 16, 2019, 5 pages.

* cited by examiner

US 10,376,195 B1

AUTOMATED NURSING ASSESSMENT

BACKGROUND

A traditional component of hospital care is the nursing assessment, in which a skilled practitioner evaluates the status of the patient. These assessments include collection of quantitative physiological parameters, such as traditional vitals like temperature, heart rate, and blood pressure, as well as qualitative assessments of the patient's mental and emotional state. These assessments are labor intensive, both in terms of initial capture time as well as the time to later transcribe the observations into patient records. As hospitals transition to electronic medical records, there have been efforts to automate the sensing and recording of physiological parameters into the medical records to reduce labor time and transcription errors. However, little progress has been made in automating the qualitative evaluation of the patient's mental and emotional state.

SUMMARY

This document describes automated nursing assessments. Automation of nursing assessments involves a nursing-assessment device that makes determinations of a person's mood, physical state, psychosocial state, and neurological state. To determine a mood and physical state of a person, video of the person is captured while they are interacting with the system. In the hospital environment, for example, the video can be captured by an autonomous mobile platform that moves from patient to patient, much as a nurse does today. In a home care environment, video can be captured while the person is positioned in front of an everyday object, such as a mirror, which they are likely to be in front of regularly, e.g., daily. The captured video is then processed according to human condition recognition techniques, which produces indications of the person's mood and physical state, such as whether the person is happy, sad, healthy, sick, and so on.

In addition to mood and physical state, the person's psychosocial and neurological state are also determined while they are positioned in front of the everyday object. To do so, questions are asked of the person. These questions are determined from a plurality of psychosocial and neurological state assessment questions, which include queries regarding how the person feels, what the person has been doing, and so on. The determined questions are asked of the person by being output audibly via speakers or visually in a display of the nursing-assessment device. The person's responses can be received and then analyzed. The analysis involves processing the received responses according to psychosocial and neurological state assessment techniques to produce indications of the person's psychosocial and neurological state.

Given these determinations, a nursing assessment report is generated that indicates some of the person's mood, physical state, psychosocial state, and neurological state. A benefit of these techniques is that they enable the general condition of a person to be assessed regularly because they can be performed in the home environment. When implemented in the hospital environment, these techniques can also free up medical professionals from having to manually perform nursing assessments and allow data to automatically populate patient electronic medical records.

This summary is provided to introduce simplified concepts concerning the techniques, which are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices for automated nursing assessments are described with reference to the following drawings. The same numbers are used throughout the drawings to reference like features and components.

DETAILED DESCRIPTION

Overview

Figure 1:
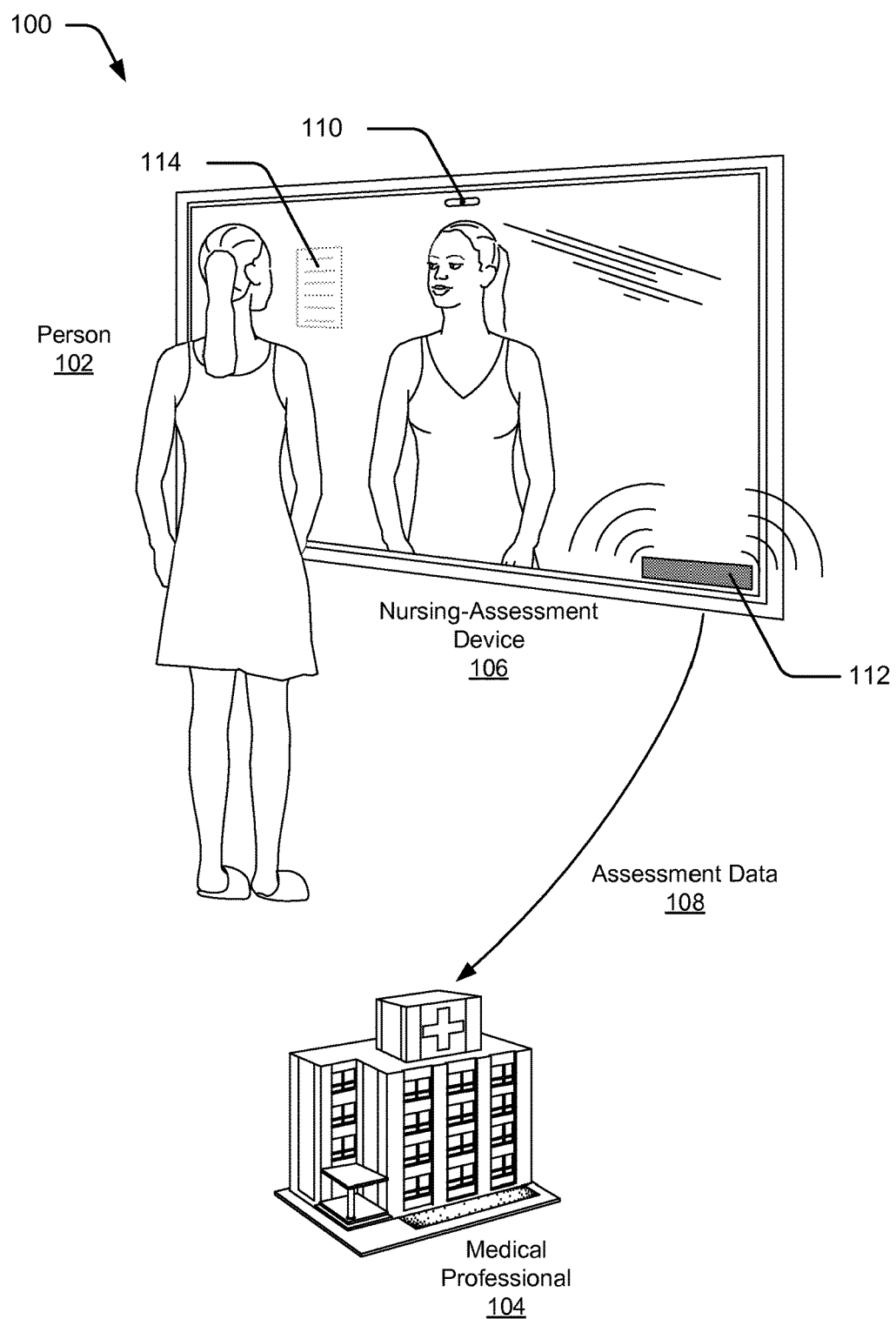
FIG. 1 illustrates an example environment in which the techniques can be implemented.

This document describes techniques using, and devices enabling, automated nursing assessments. Through use of these techniques and devices, a nursing assessment can be generated for a person without consuming a nurse's time. The automated nursing assessment report can include information indicative of a person's mood, physical state, psychosocial state, and neurological state. As used herein, the term "mood" refers to an emotional state of a person, such as whether the person is happy, sad, mad, happy but feigning sadness, sad but feigning happiness, thoughtful, and so forth. The term "physical state" refers to a condition of a person's tangible body, such as basic vital signs like temperature, heart rate, respiration rate, and blood pressure, or whether the person is sick, they are limping on their left side, their skin is pale in comparison to their base skin tone, their skin is flushed in comparison to their base skin tone, they have a new "spot" on their skin, and so on. The term "psychosocial state" refers to how a person perceives his- or herself as well as their ability to function in a community. A person's psychosocial state can be considered a sum of a variety of different factors, such as a person's stressors, symptoms the person is having, whether the person has thoughts of suicide or harming others, the person's thoughts of him- or herself, and so on. The term "neurological state" refers to a condition of a person's mental status, function of the person's cranial nerves (including vision), strength, coordination, reflexes, sensation, and so forth.

Through wide application of these techniques, an accurate assessment of a person's health can be made in the absence of a health care professional. A system capable of automating nursing assessments has many foreseeable benefits. For example, such a system can give nurses more time to perform other, more directly beneficial treatments. Nursing assessments may be performed more frequently, providing improved care and trending. Moreover, an automated system may be deployed outside of a hospital or medical practitioner's office in applications such as nursing homes or home health care to reduce costs, improve care, and reduce patient and family member inconvenience.

By way of one example in the home environment, a person can be positioned in front of an everyday object, such as a mirror, that is configured as a nursing-assessment device to include a camera, speakers, microphone, and computing resources. When it is detected that the person is positioned in front of the mirror, the camera can be employed to capture video of the person. By processing the video according to human condition techniques, a mood and physical state of the person can be determined. To maintain the privacy of the person, the processing can be performed locally by the computing resources and without communicating the captured video over a network to a remote computing device. By so doing, the captured video is not exposed to remote computing devices. In addition to determining the mood and physical state, psychosocial and neurological states are also determined while the person is positioned in front of the mirror. These states can be determined by audibly asking the person via the speakers a series of questions, such as queries regarding how the person feels, what the person has been doing, and so on. The person's verbal responses to these questions are captured via the microphone and processed to determine their psychosocial and neurological states. Additionally, the system can ask the person to perform specific motions or tasks and assess the response. A nursing assessment report that indicates one or more of the person's mood, physical state, psychosocial state, and neurological state can then be generated.

This is but one simple example of ways in which automated nursing assessments can be performed, other examples and details are provided below. This document now turns to an example environment, after which example automated nursing assessment devices and methods, and an example computing system are described.

Example Environment

FIG. 1 is an illustration of an example environment 100 in which automated nursing assessments can be employed. Environment 100 illustrates a person 102 that is the subject of an automated nursing assessment, as well as a medical professional 104 that, in some cases, will receive a report of the nursing assessment. This example employs nursing-assessment device 106 that is capable of making determinations as to the person 102's mood, physical state, psychosocial state, and neurological state. In the particular example of FIG. 1, the nursing-assessment device 106 is configured as a platform that includes a mirror, however other configurations are contemplated. Other configurations of the nursing-assessment device 106 for automating nursing assessments are illustrated in later figures.

Assessment data 108 is communicable from the nursing-assessment device 106 to other entities, such as the medical professional 104, some other computing device remote from the nursing-assessment device (not shown), and so on. The assessment data 108 can include data indicative of results of an automated nursing assessment—one performed by the nursing-assessment device 106. The results can be configured, for example, as a report that describes the person 102's mood, physical state, psychosocial state, and neurological state at the time of the assessment. The assessment data 108 can also include a request for a live health care professional to follow up with the person 102, such as when the person 102 requests, during or after an assessment, that a live health care professional follow up with them, or when the results of the assessment indicate a condition for which a live health care professional is to contact the person 102.

Although the assessment data 108 is capable of including information about the person 102's mood, physical state, psychosocial state, and neurological state, some data used to determine these states can be excluded from the assessment data 108 to maintain the privacy of the person 102. To determine the mood and physical state of the person 102, for example, the nursing-assessment device 106 captures and analyzes video of the person. When the nursing-assessment device 106 is configured as a platform that includes a mirror, as in FIG. 1, which could be located in the person 102's bathroom, the video captured of the person 102 may be content they do not want seen by others, e.g., it may include the person 102 in a state of undress. As such, the captured video may be processed locally by the nursing-assessment device 106 to determine the mood and the physical state of the person 102, but be excluded from any of the assessment data 108 that is communicated to the medical professional 104.

By way of example, a default set up of the nursing-assessment device 106 may correspond to maintaining and analyzing captured videos and images locally as well as excluding them from the assessment data 108 that is communicated from the nursing-assessment device 106. Nonetheless, the person 102 may be provided an option during set up of the nursing-assessment device 106 (or sometime after) that allows captured video and images to be communicated from the nursing-assessment device 106. Such captured videos and images may provide valuable information to the medical professional 104 that enables a condition of the person 102 to be assessed that simply cannot be assessed using the indications of mood and physical state alone. To this extent, the person may select to optionally have the captured videos and images withheld from communications, or to allow the captured videos and images to be communicated. The techniques described herein may also provide the option to withhold or allow captured videos and images to be sent on a per-communication basis. Prior to communicating a nursing assessment report to the medical professional 104, for example, the nursing-assessment device 106 may indicate to the person that it is recommended one or more images captured during the assessment be sent to the medical professional 104 for further review. The person 102 may then select whether or not they will allow those images to be included along with the particular nursing assessment report that is communicated to the medical professional 104.

Generally, the nursing-assessment device 106 represents functionality to conduct a nursing assessment of the person 102 and to generate data (e.g., a report) indicative of the results. To assess the person 102, the nursing-assessment device 106 analyzes video captured of the person 102 and responses of the person 102 to questions output by the nursing-assessment device 106. As shown with the example environment 100, the nursing-assessment device 106 can be configured to include a camera 110, a speaker 112, and a display 114. As is discussed below, the nursing-assessment device 106 employs the camera 110 to capture videos or images of the person 102. The nursing-assessment device 106 employs the speaker 112 and the display 114 to output queries to the person 102 for assessing their psychosocial and neurological states, as described in detail herein below.

As is also shown in the example environment 100, the nursing-assessment device 106 can be configured as, or as part of, an everyday object. By "everyday" object, it is meant an object that the person 102 is likely to interact with, or be positioned near, on a regular basis, e.g., daily. Using the mirror platform as an example, most people spend time each day in front of some mirror—oftentimes their bathroom mirror. People brush their teeth in front of bathroom mirrors, floss, wash their face, brush or comb their hair, put on makeup, and put in contacts, for example. While these activities are performed, a nursing assessment can also be conducted. Video of the person 102 can be captured by the camera 110 and analyzed, for instance, while the person 102 brushes their teeth in front of the mirror platform. Further, questions can be audibly output over the speaker 112 for the person 102 to answer. Although not shown in the example environment 100 of FIG. 1, the nursing-assessment device 106 is also configured with a microphone to capture verbal answers of the person 102 to the questions output. By configuring the nursing-assessment device 106 as, or as part of, an everyday object, nursing assessments can be conducted in a manner that departs just minimally from the normal course of the person 102's life.

Figure 2:
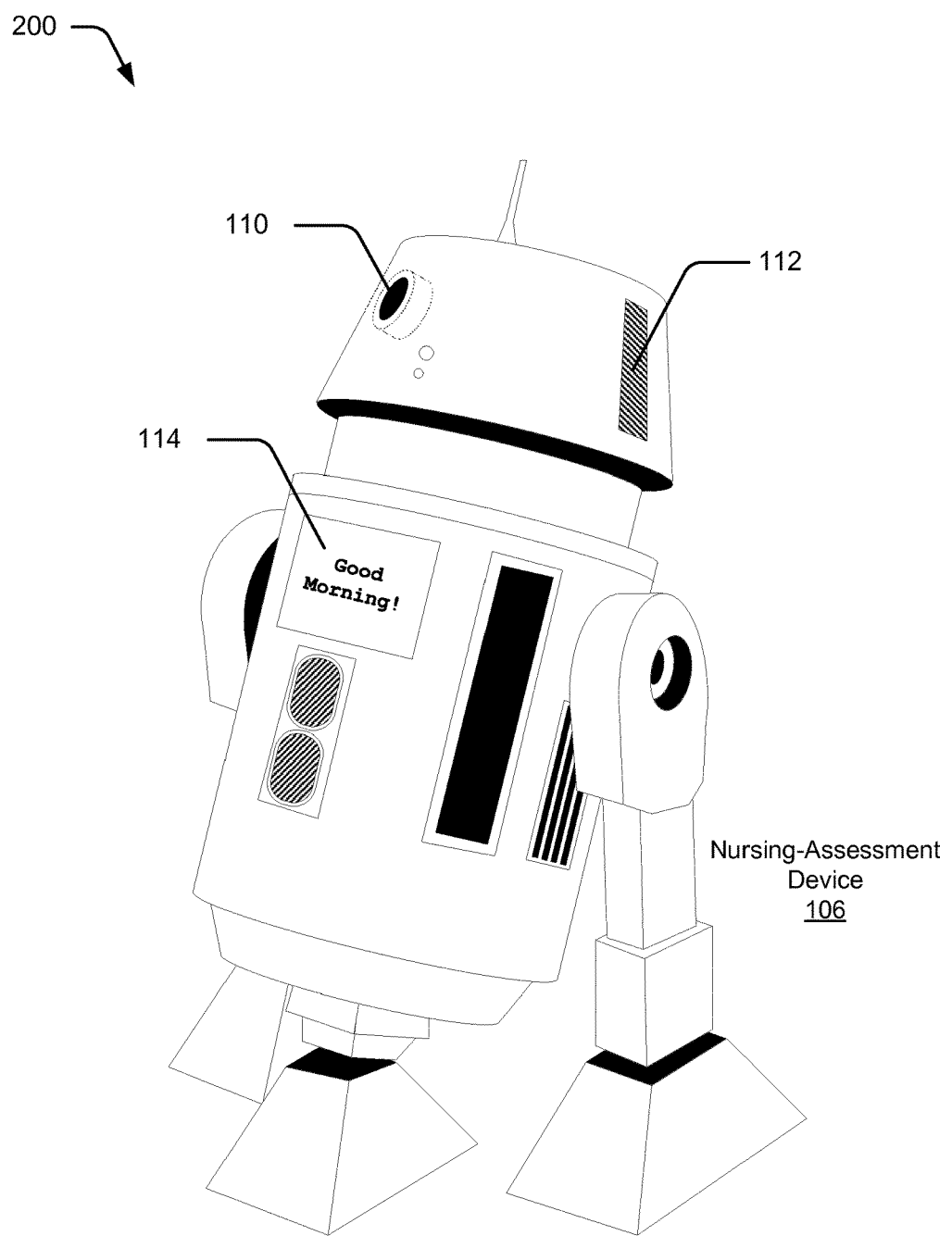
FIG. 2 illustrates an example nursing-assessment device configured as a mobile platform capable of traveling between patients to conduct nursing assessments.

Alternatively, the nursing assessment device 106 can be configured as part of a mobile platform, capable of traveling from patient to patient. FIG. 2 is an illustration of an example configuration 200 of the nursing-assessment device 106 as a mobile platform that is capable of traveling between patients to conduct nursing assessments. In a hospital environment, the mobile platform may thus perform "rounds" by moving from one patient to the next much like a traditional nurse. As part of the interactions with patients, the platform may dispense items, such as food, water, or other conveniences, and assess the response of the patients.

Figure 3:
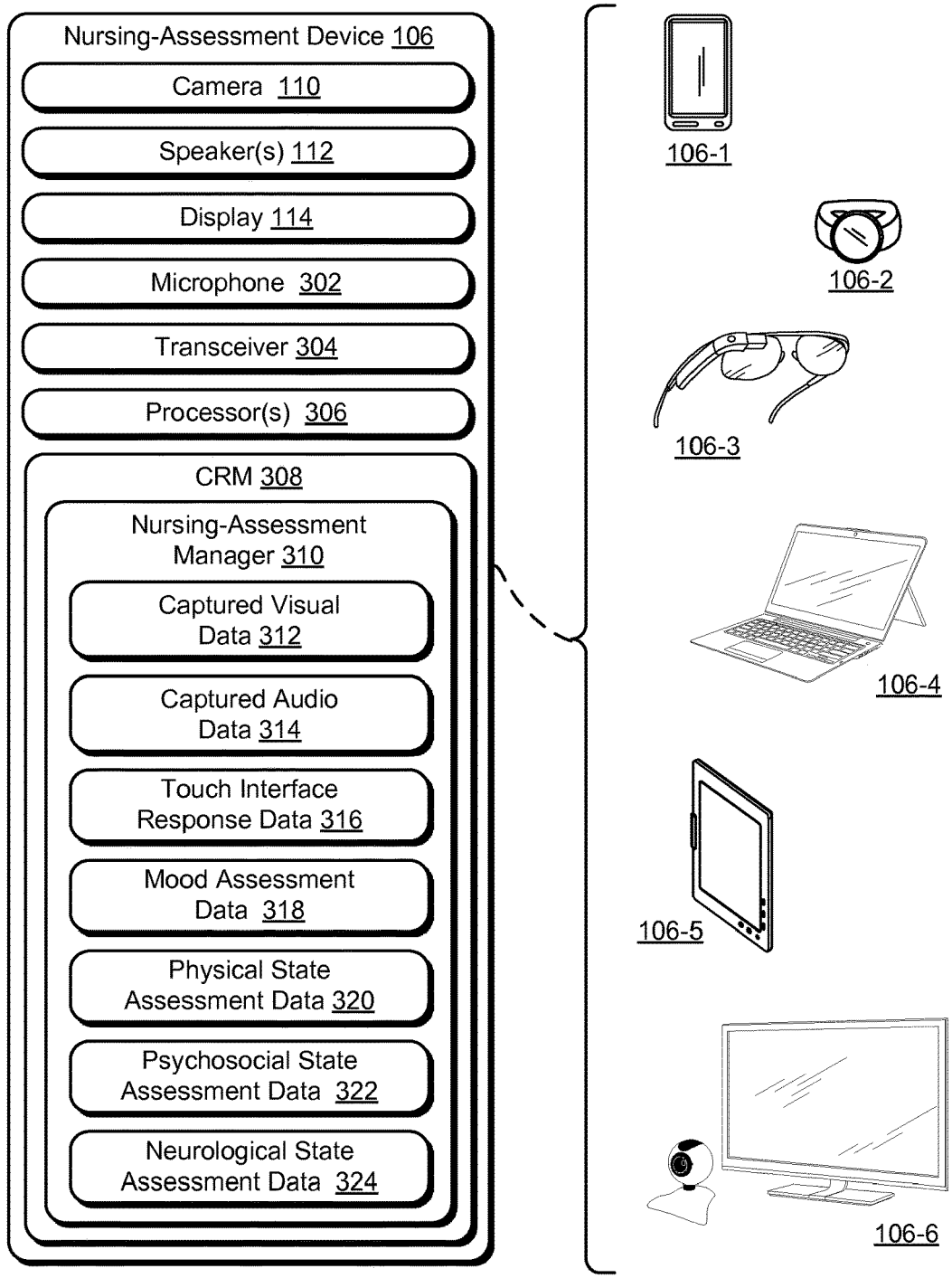
FIG. 3 illustrates an example nursing-assessment device of FIGS. 1 and 2.

With regard to the example nursing-assessment device 106 of FIGS. 1 and 2, consider a detailed illustration in FIG. 3. The nursing-assessment device 106 can also be implemented as one or a combination of various devices, here illustrated with six examples: a smartphone 106-1, a computing watch 106-2, computing spectacles 106-3, a laptop 106-4, a tablet computer 106-5, and a desktop coupled to a web cam 106-6, though other computing devices and systems, such as a netbook, a set-top box, or an autonomous mobile platform as illustrated in FIG. 2 may also be used. In some embodiments the techniques operate, in whole or in part, through a remote device. The remote computing device can be configured as a server, for example. In such cases, some computing can be forgone locally, e.g., through a communication device having limited computing operations or even directly from devices 106 to the server. With regard to everyday-object configurations, in addition to a platform that includes a mirror, the nursing-assessment device 106 can be configured as, or as part of, a platform implemented through a shower, an automobile, a chair, a treadmill, and so forth. The nursing-assessment device 106 may also be configured in a variety of other ways without departing from the spirit or scope of the techniques described herein.

The nursing-assessment device 106 includes or is able to communicate with the camera 110, the speaker 112, the display 114 (six are shown in FIG. 3, a microphone 302, a transceiver 304, one or more processors 306, and computer-readable storage media 308 (CRM 308). The transceiver 304 is capable of sending and receiving data directly or through a communication network, such as the assessment data 108 from the devices 106 through a local area, wide area, personal area, cellular, or near-field network.

The camera 110 represents functionality of the nursing-assessment device 106 to capture video of a scene, such as one that includes the person 102. In addition to capturing video, the camera 110 may be capable of capturing still images, zooming in or out to capture video and still images, and the like. With reference to the example environment 100, the mirror platform may include a cutout within which the camera 110 can be disposed. Alternately, the mirror platform may be configured as a one-way mirror and the camera 110 may be located behind the one-way mirror to capture video of the person 102 through the mirror. The camera 110 may also be positioned above, below, or to the side of the mirror. Regardless of how the camera 110 is integrated with the nursing-assessment device 106, it can be employed by the nursing-assessment device 106 to capture video of the person 102 to determine their mood and physical state.

The speaker 112 represents functionality of the nursing-assessment device 106 to audibly output sounds, such as questions used to determine psychosocial and neurological states of the person 102. The nursing-assessment device 106 may be configured with one or multiple speakers. In addition to audibly outputting questions, the speaker 112 can output other audio, such as music, telephone calls, radio shows, and the like. With reference to the example environment 100, the mirror platform may include a cutout within which the speaker 112 can be disposed. The speaker 112 may also be positioned above, below, or to the side of the mirror. In some instances, the speaker 112 may simply be installed in a same room as the mirror. Regardless of how the speaker 112 is integrated with the nursing-assessment device 106, it can be employed by the nursing-assessment device 106 to audibly output questions to the person 102 as part of determining their psychosocial and neurological states.

In concert with the speaker 112, the microphone 302 functions to capture sounds, such as verbal answers of the person 102 to the psychosocial and neurological questions that are output via the speaker 112. The nursing-assessment device 106 may be configured with one or multiple microphones, and they may be directional. Although the microphone 302 is not depicted in the example environment 100, it may be incorporated with the nursing-assessment device 106 in such a way as to capture the verbal responses of the person 102 without requiring action of the person 102 other than to speak their answers. By way of example, the person 102 may simply give their verbal responses without having to pick up the microphone 302 and speak directly into it, lean into a spot where the microphone 302 is located and speak directly into it, and so on. Nevertheless, if the person 102 chooses to position the nursing-assessment device 106 or themselves in such a way as to speak directly into the microphone 302, the person 102's responses are still captured. Regardless of how the microphone 302 is integrated with the nursing-assessment device 106, it can be employed by the nursing-assessment device 106 to capture the person 102's verbal responses to the psychosocial and neurological assessment questions.

The display 114 represents functionality of the nursing-assessment device 106 to visually output information, such as questions used to determine the psychosocial and neurological states of the person 102, options that the person 102 can select to answer those questions, contact information of the medical professional 104, daily reminders (e.g., a to-do list), news and entertainment content, and so forth. The display 114 also represents functionality of the nursing-assessment device 106 to receive touch input, such as when the person touches a displayed option to answer one of the psychosocial and neurological state assessment questions. With reference to the example environment 100, the display 114 may comprise a portion of the mirror that is configured to display a user interface and is also configured with touchscreen functionality. When not being used to display a user interface, the portion configured as the display 114 may function in a similar manner as the rest of the mirror and simply reflect the environment in which it is placed. Alternately, the entire mirror may be configured for display and with touchscreen functionality. To this extent, the psychosocial and neurological state assessment questions and answering options can be displayed in a variety of locations on the mirror. Regardless of how the display 114 is integrated with the nursing-assessment device 106, it can be employed by the nursing-assessment device 106 to visually output questions to the person 102 and to receive their answers using touchscreen functionality.

The capability of the nursing-assessment device 106 to employ the camera 110, the speaker 112, the display 114, and the microphone 302 is represented by the nursing-assessment manager 310, which is embodied on the CRM 308. The nursing-assessment manager 310 also has access to captured visual data 312, which includes videos and images output by the camera 110. Captured audio data 314 represents the data that results when the verbal responses to the psychosocial and neurological state assessment questions are captured by the microphone 302 and converted into some digital audio format. In a similar fashion, touch interface response data 316 represents the input data that results from the person 102 answering the psychosocial and neurological state assessment questions using touch functionality of the display 114, such as data indicating an option selected to answer questions or text entered to answer questions. Further, the nursing-assessment manager 310 includes or has access to mood assessment data 318, physical state assessment data 320, psychosocial state assessment data 322, and neurological state assessment data 324, including access to electronic medical records for retrieving diagnosed conditions or past treatment, and access to past data for guiding the interactive portion of the assessment to focus on areas of concern. The mood assessment data 318, the physical state assessment data 320, the psychosocial state assessment data 322, and the neurological state assessment data 324 indicate the determinations made by the nursing-assessment manager 310 as a result of analyzing the captured visual data 312, the captured audio data 314, and the touch interface response data 316.

Accordingly, the nursing-assessment manager 310 represents functionality to analyze the captured visual data 312, the captured audio data 314, and the touch interface response data 316 that is gathered as part of conducting a nursing assessment of the person 102. Broadly speaking, a nursing assessment corresponds to a period of time during which the camera 110 captures video of the person 102 and during which questions are output to the person and answers are received. Generally, the length of an assessment corresponds to an amount of time that the camera 110 is employed to capture video of the person 102 that is sufficient to determine the mood and physical state of the person as well as the time it takes to answer questions that are sufficient to determine the psychosocial and neurological states of the person 102. In some embodiments, the nursing-assessment device 106 is capable of alerting the person 102 when a sufficient amount of video has been captured and a sufficient number of questions have been answered to end the assessment. By way of example, the nursing-assessment device 106 can be configured to alert the person 102 audibly by outputting a message through the speaker 112 such as "Thank you for your answers. Your nursing assessment is complete. Have a nice day." The nursing-assessment device 106 can also be configured to alert the person 102 visually by outputting a similar message via the display 114.

In one example, the nursing-assessment manager 310 initiates an automated nursing assessment by employing the camera 110 to capture video of the person 102. The nursing-assessment manager 310 can initiate the assessment in response to detecting the presence of the person 102. With reference to the example environment 100, the nursing-assessment manager 310 may detect that the person 102 is positioned in front of the mirror of the platform, e.g., using motion detection techniques. Furthermore, the nursing-assessment manager 310 can initiate the information-gathering session in response to detecting the presence of a particular person or people, such as the person 102. Given this, the nursing-assessment manager 310 is also capable of not initiating an assessment when a person is detected for whom an automated nursing assessment is not to be conducted. The nursing-assessment manager 310 may make this determination using facial recognition techniques, for example.

Still further, the nursing-assessment manager 310 may not initiate an assessment for the person 102 if one has already been conducted for the person 102 within a prescribed time period. By way of example, if nursing assessments are to be conducted for the person 102 daily and the day's nursing assessment has already been conducted, the nursing-assessment manager 310 may not initiate another assessment of the person 102. This does not preclude the nursing-assessment manager 310 from initiating an assessment for another person for whom automated nursing assessments are to be conducted and who has not yet been assessed in the current period of time, which may be the case at a hospital where more than one patient or person uses the same facilities. In any case, the frequency with which the person 102 is to be assessed can change based on the results of a previous assessment—the nursing-assessment manager 310 can determine that the person 102 is to be assessed more or less frequently. This frequency can also be changed based on a review of one or more previous assessments by the medical professional 104 and input from the medical professional 104 (e.g., via a user interface presented to the medical professional 104 in conjunction with reports of the automated nursing assessments) to increase or decrease the frequency of the assessments.

Once the camera 110 captures video or images of the person 102, the nursing-assessment manager 310 determines a mood and physical state of the person. To do so, the nursing-assessment manager 310 is capable of processing the captured visual data 312 according to one or more human condition recognition techniques. As discussed above, a person's mood refers to their emotional state and a person's physical state refers to a condition of their tangible body. The nursing-assessment manager 310 may be capable of applying the human condition recognition techniques to determine a person's mood as a result of a machine learning process in which the nursing-assessment manager 310 is trained to recognize various emotional states using visual data that corresponds to these different states. In a similar manner, the nursing-assessment manager 310 may be capable of applying the human condition recognition techniques to determine the condition of a person's tangible body as a result of a machine learning process in which the nursing-assessment manager 310 is trained to recognize various conditions of people's bodies using visual data that corresponds to these different conditions.

Based on the determined mood and physical state, the nursing-assessment manager 310 can generate the mood assessment data 318 and the physical state assessment data 320 that corresponds to these determinations. By way of example, when the nursing-assessment manager 310 determines that the person 102 is in a happy mood, it can generate data that indicates the person 102 is happy, and store this data as part of the mood assessment data 318. Similarly, when the nursing-assessment manager 310 determines that the person 102 has a limp, it can generate data that indicates the person 102 is limping, and store this data as part of the physical state assessment data 320. It should be appreciated that the nursing-assessment manager 310 may recognize more than one mood and more than one physical condition of the person 102 during a given information-gathering session. Thus, for the corresponding nursing assessment, the nursing-assessment manager 310 is capable of generating data that describes the multiple moods and physical conditions recognized. As part of the mood and physical state assessment, the nursing assessment manager 310 may ask the patient to perform various physical tasks for evaluation and assessment.

The nursing-assessment manager 310 also determines a psychosocial and neurological state of the person 102 as part of conducting a nursing assessment. To do so, the nursing-assessment manager 310 asks the person 102 a variety of psychosocial and neurological state assessment questions and analyzes the person 102's answers to those questions. Prior to asking questions, however, the nursing-assessment manager 310 determines which psychosocial and neurological state assessment questions to ask. By way of example, the nursing-assessment manager 310 may select the particular questions to ask from a database of potential psychosocial and neurological state assessment questions. Further, the nursing-assessment manager 310 may select the particular questions based on a variety of factors, such as the person 102's determined mood and physical state, results of previously-conducted nursing assessments, questions that the medical professional 104 associated with the person 102 has selected (e.g., via a user interface) to have asked, answers given by the person 102 earlier in the current nursing assessment, and so forth.

The nursing-assessment manager 310 is capable of asking the person the determined questions in different ways through different interfaces of the nursing-assessment device 106. For example, the nursing-assessment manager 310 may cause the questions to be audibly output via the speaker 112. To this extent, the person 102 may hear the questions asked. To respond, the person 102 may simply answer the questions verbally. In this case, the person 102 has a conversation with the nursing-assessment device 106. The person 102's verbal responses may be captured using the microphone 302 and result in the captured audio data 314.

Figure 4:
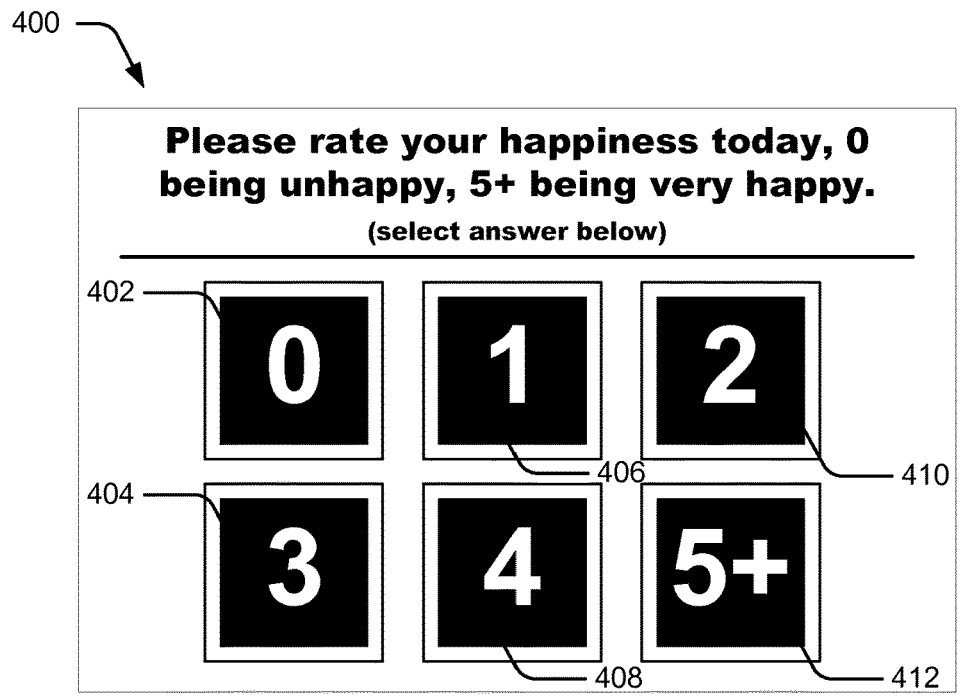
FIG. 4 illustrates an example of a user interface presented during an automated nursing assessment to capture information about a person's psychosocial or neurological state.
Figure 5:
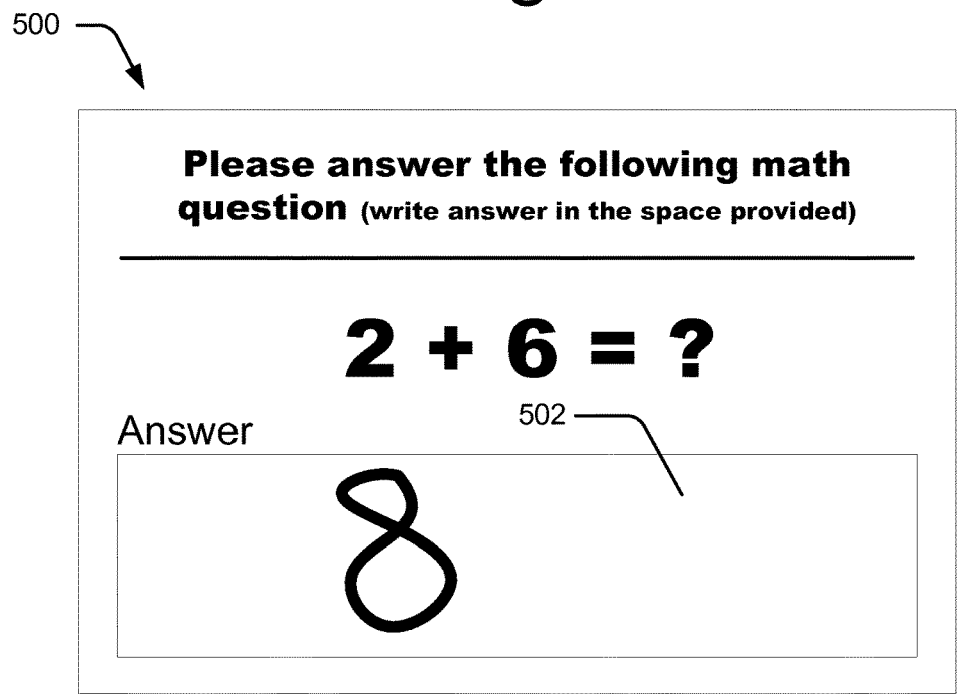
FIG. 5 illustrates an example of another user interface presented during an automated nursing assessment to capture information about the person's psychosocial or neurological state.

The nursing-assessment manager 310 may also cause the questions to be visually output via the display 114. For context, consider FIGS. 4 and 5, which illustrate examples of user interfaces that can be presented during an automated nursing assessment to capture information about the person's psychosocial or neurological state.

The example user interface 400 includes an example of a psychosocial state assessment question and selectable answers 402, 404, 406, 408, 410, 412. The user interface 400 is capable of being presented to the person 102 via the display 114. The selectable answers 402, 404, 406, 408, 410, 412 are selectable by the person 102 using touch functionality. In other words, the person 102 can touch the portion of the display 114 that corresponds to their answer.

In contrast, the example user interface 500 includes a freeform answer portion 502 that enables a person to write an answer to the example neurological state assessment question. The user interface 500 is also capable of being presented to the person 102 via the display 114. The freeform answer portion 502 enables a person to write an answer to a presented question using their finger or a stylus. By way of example, the person 102 may trace their finger in the shape of an "8" at the portion of the display 114 that corresponds to the freeform answer portion 502. Touch functionality of the display 114 enables this input to be detected and a graphic produced that is indicative of the person 102's writing. The display 114 can also display a graphic indicative of the 8-shape traced by the person, as is shown in the example user interface 500.

This functionality allows the person 102 to read the questions asked and not merely to hear them and respond verbally. To respond to visually presented questions, the person 102 may input their answers using touch functionality or may respond verbally as with the audibly output questions. When causing the questions to be visually output, the nursing-assessment manager 310 may also cause possible answers to be displayed with the questions. In this way, the person 102 may select an answer to a question by touching a corresponding graphic, such as the answer itself or a button near the answer. Alternately or in addition, the display 114 may enable the person 102 to "write" an answer. By way of example, a keyboard may be presented via the display 114 that the person 102 can use to type their answer. Alternately, the person 102 may be able to handwrite an answer on the display 114 using a finger or a stylus. In any case, the person 102 may respond to the asked psychosocial and neurological state assessment questions in a variety of ways without departing from the spirit or scope of the techniques described herein.

Regarding particular questions asked to the person 102, the nursing-assessment manager 310 may select questions for determining the psychosocial state that prompt the person 102 to explain how the person 102 perceives his- or herself as well as their ability to function in a community. The questions may prompt the person 102 to explain, for example, stressors, symptoms the person 102 is having, whether the person 102 has thoughts of suicide or harming others, the person 102's thoughts of him- or herself, and so on. For determining the neurological state, the nursing-assessment manager 310 may select questions that prompt the person to explain the condition of their mental status, function of the cranial nerves (including vision), strength, reflexes, sensation, and so on. By way of example, neurological state assessment questions selected by the nursing-assessment manager 310 may include asking the person 102 to repeat sentences, solve simple mathematical problems, and so on.

Based on the person 102's answers to the questions, the nursing-assessment manager 310 determines their psychosocial and neurological states. By way of example, the nursing-assessment manager 310 may analyze the person 102's answers according to one or more psychosocial and neurological state assessment techniques, which may map certain answers to particular psychosocial or neurological states. In addition, the nursing-assessment manager 310 may analyze characteristics of the manner in which questions are answered. By way of example, when the person 102 answers questions verbally, characteristics of the person 102's voice or the way in which they speak may be analyzed. The nursing-assessment manager 310 may note, for instance, whether the person is slurring their words, whether their speech is relatively slow, whether they are answering loudly, and so forth. In a similar manner, characteristics of the person 102's touch input can be analyzed when questions are answered via the display 114. The nursing-assessment manager 310 can determine whether the person 102's hand is shaky when selecting a graphic or writing an answer to a question, whether the person 102 writes an answer slowly, whether the person consistently selects an off-center portion of a graphic for answering questions, and so forth. An analysis of the manner in which the person 102 answers the questions (e.g., "how" the person answers the questions in contrast to "what" is answered) can also provide insight into their psychosocial and neurological states. Based on the determined psychosocial and neurological states, the nursing-assessment manager 310 can generate the psychosocial state assessment data 322 and the neurological state assessment data 324 that corresponds to these determinations.

For example, the nursing-assessment manager 310 can generate a few sentences or terms that describe the person 102's determined psychosocial state, and store this data as part of the psychosocial state assessment data 322. Similarly, the nursing-assessment manager 310 can generate a few sentences or terms that describe the person 102's determined neurological state, and store this data as part of the neurological state assessment data 324. Instead of sentences or terms, the nursing-assessment manager 310 can generate other data that is suitable for describing the person 102's psychosocial and neurological states without departing from the techniques described herein.

The determined mood, physical state, psychosocial state, and neurological state, which are captured in the mood assessment data 318, the physical state assessment data 320, the psychosocial state assessment data 322, and the neurological state assessment data 324, are then used by the nursing-assessment manager 310 to generate a report of the nursing assessment. The report generated by the nursing-assessment manager 310 includes information that indicates the person 102's mood, physical state, psychosocial state, and neurological state at the time of the automated nursing assessment.

These reports may be configured for display as part of a user interface, such as via a computing device of the medical professional 104. The report is also capable of being communicated, once generated, from the nursing-assessment device 106 over a network and to the computing device associated with the medical professional 104. Further, the report may be communicated to other entities, such as to a service that maintains medical records of the person 102. By communicating just the report, and not the data from which the report is generated, the nursing-assessment manager 310 can ensure that videos of the person 102 are not communicated to a remote entity and that the privacy of the person is thus maintained.

As noted above, the reports generated by the nursing-assessment manager 310 indicate the mood, physical state, psychosocial state, and neurological state of the person 102 at the time that an automated nursing assessment was conducted. Thus, a report and the information gathered and generated for a particular nursing assessment can be associated with a time that the nursing assessment was conducted. The captured visual data 312, for example, can be associated with a time when it was captured, e.g., the nursing-assessment manager 310 can associate a timestamp with the captured video. The mood assessment data 318 and the physical state assessment data 320 that are generated from the captured visual data 312 can also be associated with the time. In a similar manner, the captured audio data 314, the touch interface response data 316, the psychosocial state assessment data 322, and the neurological state assessment data 324, may also be associated with the time.

Visual data that is captured at a different time, say after the above-discussed captured visual data 312 can be associated with a different time. Accordingly, the mood assessment data 318 and the physical state assessment data 320 generated from this second portion of the captured visual data can be associated with the different time. The captured audio data 314, the touch interface response data 316, the psychosocial state assessment data 322, and the neurological state assessment data 324, captured and generated during their same automated nursing assessment can also be associated with the different time. In so doing, the reports generated for the nursing assessments, as well as the mood assessment data 318, the physical state assessment data 320, the psychosocial state assessment data 322, and the neurological state assessment data 324 can be compared over time.

Based on a comparison of the person's mood, physical state, psychosocial state, and neurological state determined at different times, a trend in the person 102's health can be determined. For example, nursing assessments conducted twice a day over a week can be compared to determine a trend in the person 102's health for the week. The physical state assessment data 320 over the week may indicate an improvement or worsening of a medical condition, for example. Based on the trend (e.g., the determined improvement or worsening), a medical professional may be able to make other assessments regarding the person 102, such as to the effectiveness of treatments being administered to the person 102.

When a nursing assessment of the person 102 is conducted, the nursing-assessment manager 310 may optionally communicate a request for a live health care professional to follow up with the person. The nursing-assessment manager 310 may do so based simply on the results of the nursing assessment, e.g., when the results indicate a worsening of some condition of the person. Alternately in addition, the nursing-assessment manager 310 may do so based on a request from the person 102 to have a live health care professional contacted. By way of example, at the end of conducting a nursing assessment, the nursing-assessment manager 310 may cause a question to be output via the speaker 112 asking if the person 102 would like to have a live health care professional follow up with them. If the person 102 answers "yes", the nursing-assessment manager 310 can then generate and communicate a request for the live health care professional to follow up with the person 102. The nursing-assessment manager 310 may also cause a prompt to be output on the display 114 such as "Would you like a live nurse to follow up with you? Select YES or NO." Responsive to the person selecting "YES", the nursing-assessment manager 310 can generate and communicate a request for the live health care professional to follow up with the person 102.

Based on the request, a live health care professional may call the person 102 at a given number to discuss the reasons they wanted to be contacted by a nurse. A live health care professional may also be connected for conversation with the person 102 through the nursing-assessment device 106. Thus the nursing-assessment device 106 may act as a telephone. The live health care professional's voice may be output over the speaker 112, and the person 102's voice may be captured by the microphone 302 and sent to the live health care professional. In this way, a conversation between the live health care professional and the person 102 may be conducted.

These and other capabilities, as well as ways in which entities of FIGS. 1-5 act and interact, are set forth in greater detail below. These entities may be further divided, combined, and so on. The environment 100 of FIG. 1 and the detailed illustrations of FIGS. 2-5 illustrate some of many possible environments capable of employing the described techniques.

Example Methods

Figure 6:
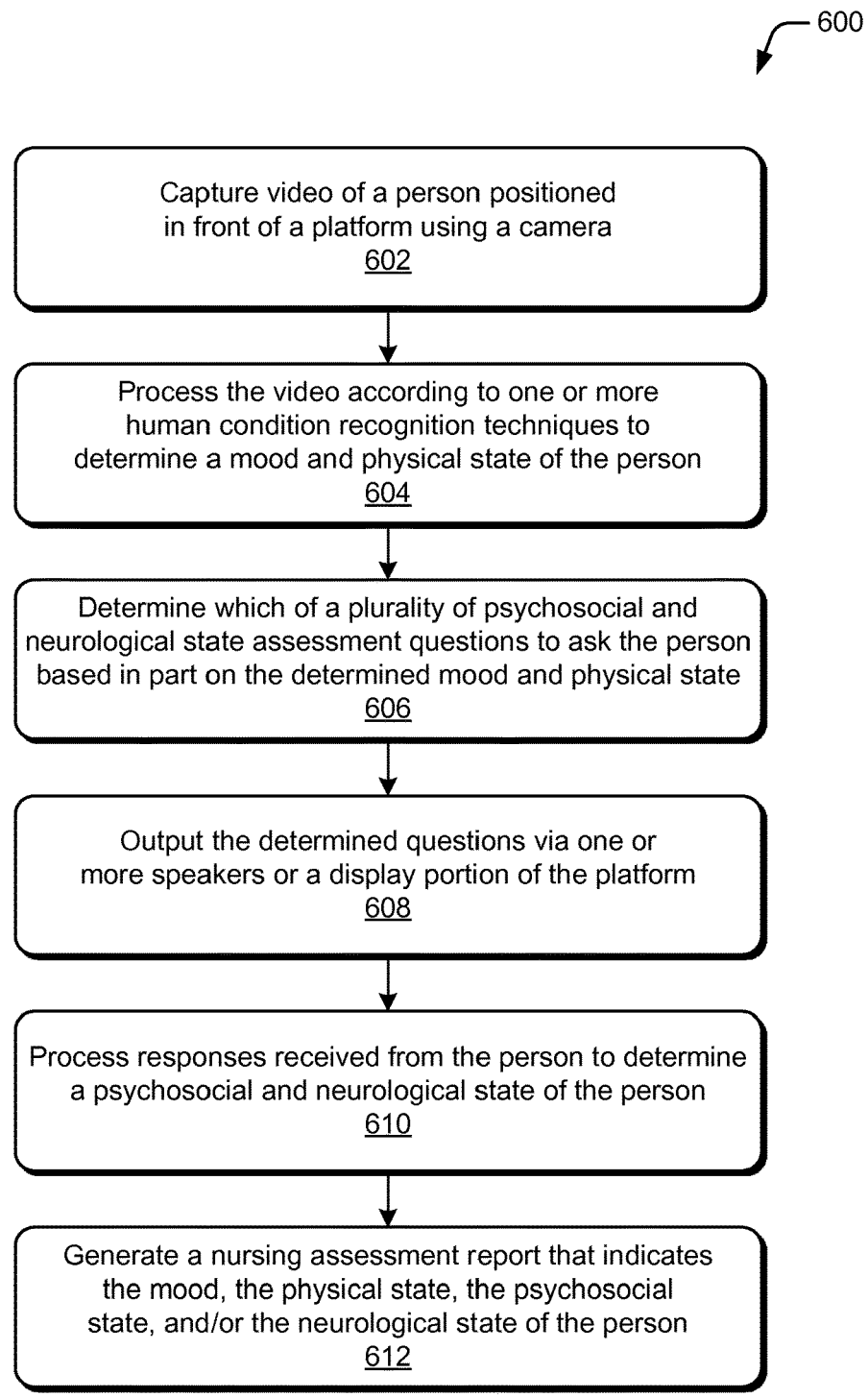
FIG. 6 illustrates a method for generating a nursing assessment through an automated determination of a person's mood, physical state, psychosocial state, and neurological state.
Figure 7:
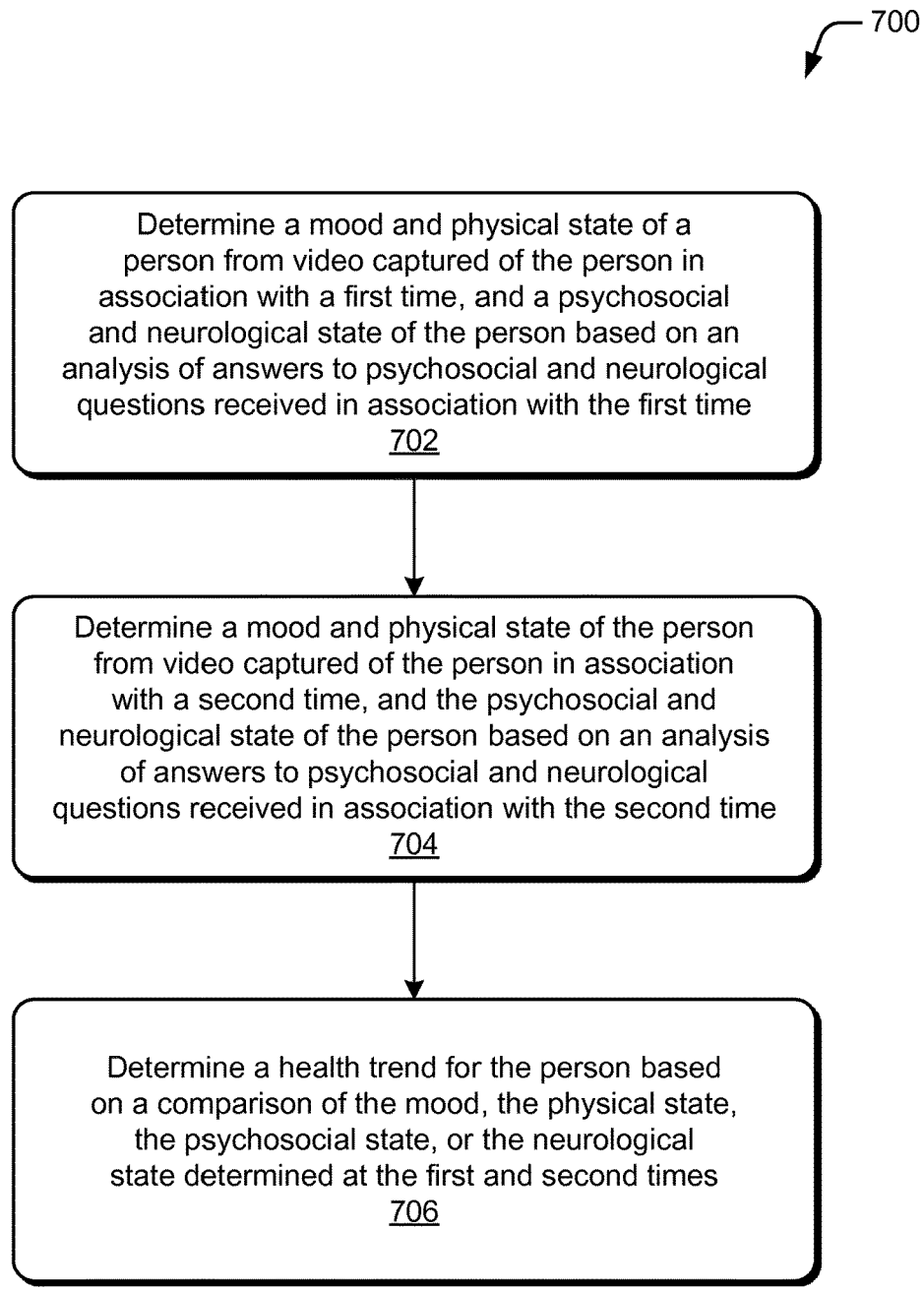
FIG. 7 illustrates a method to determine a trend in a person's health based on a comparison of their mood, physical state, psychosocial state, and neurological state determined at different times.

FIGS. 6 and 7 depict methods enabling or using automated nursing assessments. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIGS. 2-5, reference to which is made for example only. The techniques are not limited to performance by one entity or multiple entities operating on one device.

FIG. 6 depicts a method 600, which describes manners in which to generate a nursing assessment through an automated determination of a person's mood, physical state, psychosocial state, and neurological state.

At 602, video is captured of a person positioned in front of a platform using a camera. Consider an example in which the nursing-assessment device 106 detects the presence of the person 102 standing in front of the platform that includes the mirror, as is the case in FIG. 1. The presence of the person 102 can be detected using a variety of techniques, such as motion detection techniques. In this example, assume also that the nursing-assessment device 106 distinguishes the person 102 from other people (e.g., using facial recognition techniques) and knows that the person 102 is due to have an automated nursing assessment conducted. As part of conducting the automated nursing assessment, the nursing-assessment manager 310 employs the camera 110 to capture video of the person 102 while standing in front of the mirror. The nursing-assessment manager 310 maintains this video as part of the captured visual data 312.

At 604, the captured video is processed according to human condition recognition techniques to determine a mood and physical state of the person. By way of example, the captured visual data 312 is processed by the nursing-assessment manager 310, embodied on the CRM 308 of the nursing-assessment device 106, to determine the mood and physical state of the person 102. In the ongoing example, the captured visual data 312 is processed by the nursing-assessment manager 310 without being communicated to a remote computing device, such as one associated with the medical professional 104. For instance, the nursing-assessment manager 310 processes the captured visual data 312 according to one or more human condition recognition techniques to recognize a mood (e.g., happy, sad, etc.) and a physical state (e.g., sick, limping, strong, good posture, etc.) of the person 102. The nursing-assessment manager 310 also generates the mood assessment data 318 and the physical state assessment data 320 that describes the person 102's mood and physical state at the time the automated nursing assessment is conducted.

At 606, a determination is made regarding which of a plurality of psychosocial and neurological state assessment questions to ask the person based in part on the determined mood and physical state. By way of example, the nursing-assessment manager 310 analyzes the mood assessment data 318 and the physical state assessment data 320 that describes the person 102's mood and physical state. The nursing-assessment manager 310 then selects questions to ask the person from a list of psychosocial and neurological state assessment questions based on the person 102's mood and physical state.

The nursing-assessment manager 310 also considers other factors in determining which psychosocial and neurological state assessment questions to ask the person 102, such as the results of previously conducted automated nursing assessments (e.g., follow up questions to determine if a condition discussed during a previous assessment has improved or worsened), answers of the person 102 to questions already asked as part of the current automated nursing assessment, input from the medical professional 104 associated with the person 102 that indicates certain questions are to be asked, and so on.

At 608, the determined questions are output via one or more speakers or a display portion of the platform. The nursing-assessment manager 310, for example, causes the questions determined at 606 to be output via the speaker 112 of the nursing-assessment device 106. The nursing-assessment manager 310 can also cause the questions determined at 606 to be visually output via the display 114. The questions output audibly via the speaker 112 and visually via the display 114 may be different questions that are better asked or more easily answered via the chosen modality. The questions output audibly via the speaker 112 and visually via the display 114 can also be the same questions such that a question output via the speaker 112 is concurrently presented to the person 102 via the display 114.

At 610, responses received from the person are processed to determine psychosocial and neurological states of the person. In response to the questions output at 608, the person 102 may answer verbally. For example, when a question is output via the speaker 112 that asks, "How many times have you been to the bathroom today?" the person 102 may verbally respond "three." Such a verbal response is captured via the microphone 302 and results in generation of at least a portion of the captured audio data 314. With regard to questions output via the display 114, the same question can be output via the display 114 and the person 102 may respond verbally as above, or may respond by making a touch selection of a graphic that represents the number three. A touch input response of this sort is received through touch functionality of the nursing-assessment device 106 and results in generation of a portion of the touch interface response data 316. The nursing-assessment manager 310 processes the captured audio data 314 and the touch interface response data 316, which are indicative of the person 102's responses, to determine the psychosocial and neurological states of the person. The nursing-assessment manager 310 also generates the psychosocial state assessment data 322 and the neurological state assessment data 324 that describes the person 102's psychosocial and neurological states at the time the automated nursing assessment is conducted.

At 612, a nursing assessment report is generated that indicates the mood, the physical state, the psychosocial state, and/or the neurological state of the person. By way of example, the nursing-assessment manager 310 generates a report that describes the mood, the physical state, the psychosocial state, and the neurological state of the person 102 at the time of the automated nursing assessment. To do so, the nursing-assessment manager 310 can access the mood assessment data 318, the physical state assessment data 320, the psychosocial state assessment data 322, and the neurological state assessment data 324 generated in conjunction with the particular nursing assessment, and combine the information represented by that data into the report. The report may be configured as a user interface that is communicable to the medical professional 104 and displayable on a computing device associated with the medical professional 104. In addition or alternately, the report can be maintained in a database that stores medical records, and can be accessed to later generate a user interface, a document for printing, and the like.

FIG. 7 depicts method 700, which describes manners in which to determine a trend in a person's health based on a comparison of their mood, physical state, psychosocial state, and neurological state as determined at different times.

At 702, a mood and physical state of a person are determined from video captured of the person in association with a first time. A psychosocial state and neurological state of the person are also determined based on an analysis of answers to psychosocial and neurological state assessment questions asked in association with the first time. By way of example, the nursing-assessment manager 310 employs the camera 110 to capture a video of the person 102 at a first time, as in act 602 of FIG. 6. The nursing-assessment manager 310 then processes the video captured at the first time to determine the mood and physical state of the person as in act 604. The nursing-assessment manager 310 also determines which of a plurality of psychosocial and neurological state assessment questions to ask the person 102 as in act 606, and outputs the determined questions as in act 608. The nursing-assessment manager 310 processes the person 102's responses to the questions to determine their psychosocial and neurological states as in act 610. The person 102's mood, physical state, psychosocial state, and neurological state determined at the first time may be captured in the physical state assessment data 320, the psychosocial state assessment data 322, and the neurological state assessment data 324 that is stored with an indication that it is associated with the first time.

At 704, a mood and physical state of the person are determined from video captured of the person in association with a second time. A psychosocial state and neurological state of the person are also determined based on an analysis of answers to psychosocial and neurological state assessment questions asked in association with the second time. The nursing-assessment manager 310 again employs the camera 110 to capture a video of the person 102 as in act 602 of FIG. 6, but this time in association with the second time. The nursing-assessment manager 310 then processes the video captured at the second time to determine the mood and physical state of the person as in act 604. The nursing-assessment manager 310 also determines which of a plurality of psychosocial and neurological state assessment questions to ask the person 102 as in act 606, and outputs the determined questions as in act 608. The nursing-assessment manager 310 processes the person 102's responses to the questions to determine their psychosocial and neurological states as in act 610. The person 102's mood, physical state, psychosocial state, and neurological state determined at the second time may be captured in the physical state assessment data 320, the psychosocial state assessment data 322, and the neurological state assessment data 324 that is stored with an indication that it is associated with the second time.

At 706, a trend in health of the person is determined based on a comparison of the mood, the physical state, the psychosocial state, and the neurological state determined at the first and second times. By way of example, the nursing-assessment manager 310 accesses the physical state assessment data 320, the psychosocial state assessment data 322, and the neurological state assessment data 324 that results from the determinations made in acts 702 and 704 from storage. The nursing-assessment manager 310 then compares the data from these two times. The comparison may indicate an improvement or worsening of any of the states, e.g., mood, physical, psychosocial, neurological. A trend in the person 102's health can be determined from the improvement or worsening of these states. Such a trend can be indicative of whether treatments being administered to the person 102 are effective. When the person 102 is taking medication for an infection, for example, the trend can indicate whether the medicine is acting to clear up the infection or whether it is failing to do so.

The preceding discussion describes methods relating to automated nursing assessments. Aspects of these methods may be implemented in hardware (e.g., fixed logic circuitry), firmware, software, manual processing, or any combination thereof. These techniques may be embodied on one or more of the entities shown in FIGS. 1, 2, 3, and 8 (computing system 800 is described in FIG. 8 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 8:
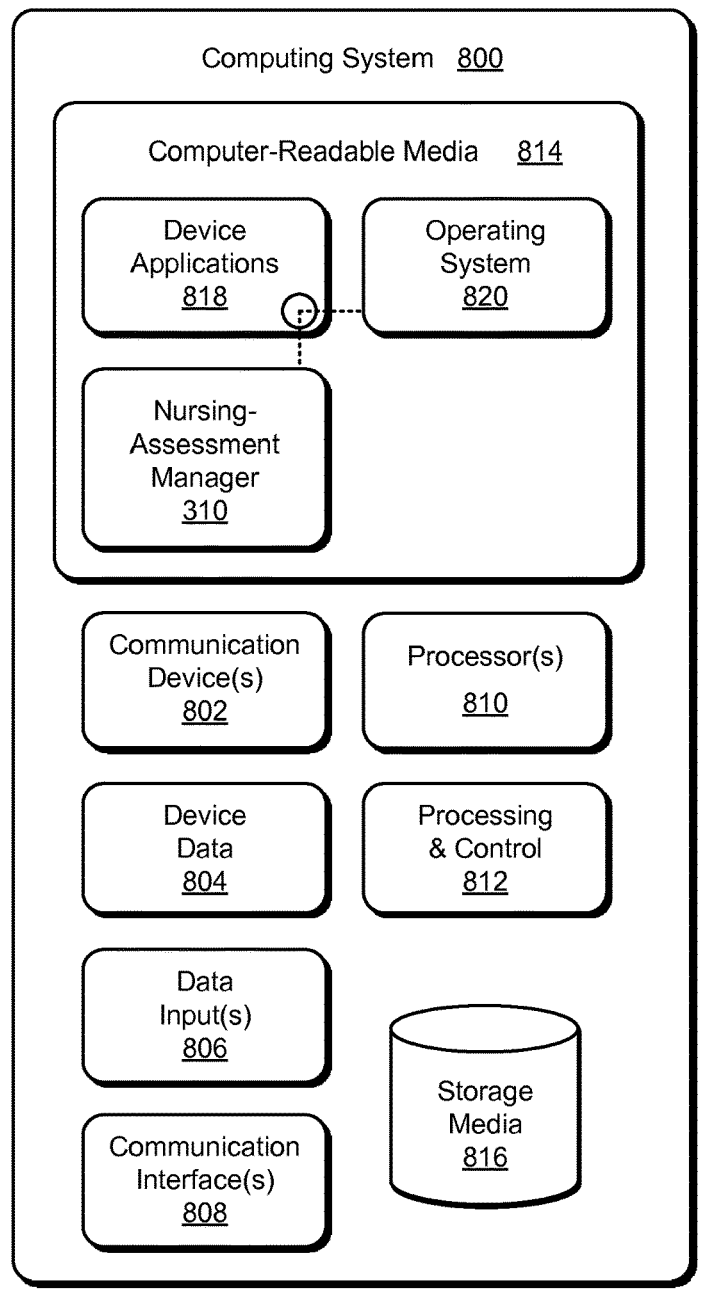
FIG. 8 illustrates an example computing system embodying, or in which techniques may be implemented that enable use of, automated nursing assessments.

FIG. 8 illustrates various components of example computing system 800 that can be implemented as any type of client, server, and/or computing device as described with reference to the previous FIGS. 1-7 to implement automated nursing assessments. In embodiments, computing system 800 can be implemented as one or a combination of a wired and/or wireless wearable device, System-on-Chip (SoC), and/or as another type of device or portion thereof. Computing system 800 may also be associated with a user (e.g., a person) and/or an entity that operates the device such that a device describes logical devices that include users, software, firmware, and/or a combination of devices.

Computing system 800 includes communication devices 802 that enable wired and/or wireless communication of device data 804 (e.g., received data, data that is being received, data scheduled for broadcast, data packets of the data, etc.). Device data 804 or other device content can include configuration settings of the device, media content stored on the device, and/or information associated with a user of the device. Media content stored on computing system 800 can include any type of audio, video, and/or image data, including complex or detailed results of automated nursing assessment acts. Computing system 800 includes one or more data inputs 806 via which any type of data, media content, and/or inputs can be received, such as human utterances, user-selectable inputs (explicit or implicit), messages, music, television media content, recorded video content, and any other type of audio, video, and/or image data received from any content and/or data source.

Computing system 800 also includes communication interfaces 808, which can be implemented as any one or more of a serial and/or parallel interface, a wireless interface, any type of network interface, a modem, and as any other type of communication interface. Communication interfaces 808 provide a connection and/or communication links between computing system 800 and a communication network by which other electronic, computing, and communication devices communicate data with computing system 800.

Computing system 800 includes one or more processors 810 (e.g., any of microprocessors, controllers, and the like), which process various computer-executable instructions to control the operation of computing system 800 and to enable techniques for, or in which can be embodied, automated nursing assessments. Alternatively or in addition, computing system 800 can be implemented with any one or combination of hardware, firmware, or fixed logic circuitry that is implemented in connection with processing and control circuits which are generally identified at 812. Although not shown, computing system 800 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Computing system 800 also includes computer-readable media 814, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Computing system 800 can also include a mass storage media device 816.

Computer-readable media 814 provides data storage mechanisms to store device data 804, as well as various device applications 818 and any other types of information and/or data related to operational aspects of computing system 800. For example, an operating system 820 can be maintained as a computer application with computer-readable media 814 and executed on processors 810. Device applications 818 may include a device manager, such as any form of a control application, software application, signal-processing and control module, code that is native to a particular device, a hardware abstraction layer for a particular device, and so on.

Device applications 818 also include any system components, engines, or managers to implement the techniques. In this example, device applications 818 include the nursing-assessment manager 310.

Conclusion

Although embodiments of techniques using, and apparatuses enabling, automated nursing assessments have been described in language specific to features and/or methods, it is to be understood that the subject of the appended claims is not necessarily limited to the specific features or methods described. Rather, the specific features and methods are disclosed as example implementations of these techniques.

What is claimed is:

1. A computer-implemented method comprising:
   capturing video of a person positioned in front of a nursing-assessment device, using a camera that is included, or associated, with the nursing-assessment device;
   processing the captured video according to one or more human condition recognition techniques by one or more computing devices to determine a mood and a physical state of the person;
   determining, by the one or more computing devices, which of a plurality of psychosocial and neurological state assessment questions to ask the person based at least in part on the determined mood and physical state of the person;
   outputting the determined questions via one or more speakers or a display portion of the nursing-assessment device;
   processing, by the one or more computing devices, responses of the person according to one or more psychosocial and neurological state assessment techniques to determine a psychosocial state and a neurological state of the person;
   generating, by the one or more computing devices, a nursing assessment report that indicates at least two of the mood, the physical state, the psychosocial state, and the neurological state of the person; and
   communicating, by the one or more computing devices, the nursing assessment report to a medical professional associated with the person.

2. The computer-implemented method as described in claim 1, further comprising:
   displaying one or more of the determined questions via the display portion of the nursing-assessment device; and
   receiving touch responses from the person via touchscreen functionality of the nursing-assessment device, the touch responses being processed according to the one or more psychosocial and neurological state assessment techniques to determine the psychosocial and neurological states of the person.

3. The computer-implemented method as described in claim 1, further comprising:
   outputting, via the one or more speakers, a message asking whether the person would like a live health care professional to be contacted to follow up with the person; and
   responsive to receiving a verbal response from the person that indicates the person would like a live health care professional to be contacted, communicating, by the one or more computing devices, a request for a live health care professional follow up with the person.

4. The computer-implemented method as described in claim 1, further comprising:
   displaying, via the display portion of the nursing-assessment device, a message asking whether the person would like a live health care professional to be contacted to follow up with the person; and
   responsive to receiving, via touchscreen functionality of the nursing-assessment device, a touch response from the person that indicates the person would like a live health care professional to be contacted, communicating, by the one or more computing devices, a request for a live health care professional follow up with the person.

5. The computer-implemented method as described in claim 1, further comprising communicating a request for a live health care professional to follow up with the person based on an analysis of the nursing assessment report, the analysis by the one or more computing devices.

6. The computer-implemented method as described in claim 1, wherein the nursing assessment report does not include the captured video or images captured by the camera that are used to determine the mood and the physical state of the person.

7. The computer-implemented method as described in claim 1, wherein the capturing, processing the captured video, determining, outputting, processing the responses, and generating are performed in response to detecting that the person is positioned in front of the nursing-assessment device.

8. The computer-implemented method as described in claim 1, wherein the capturing, processing the captured video, determining, outputting, processing the responses, and generating are not performed in response to detecting that another person is positioned in front of the nursing-assessment device.

9. The computer-implemented method as described in claim 1, further comprising causing the determined mood and physical state to be stored as part of medical records associated with the person.

10. The computer-implemented method as described in claim 1, wherein the psychosocial and neurological state assessment questions are further based at least in part on input from the medical professional.

11. A system comprising:
a camera configured to capture video of a person;
interfaces configured to output psychosocial and neurological state assessment questions to the person, the interfaces further configured to capture responses of the person;
one or more processors; and
one or more computer-readable media having instructions stored thereon that, responsive to execution by the one or more processors, implements a nursing-assessment manager configured to:
process the captured video according to one or more human condition recognition techniques to determine a mood and a physical state of the person;
determine which of the psychosocial and neurological state assessment questions to ask the person based at least in part on the determined mood and physical state of the person;
process the responses of the person captured by the interfaces according to one or more psychosocial and neurological state assessment techniques to determine a psychosocial state and a neurological state of the person;
generate a nursing assessment report that indicates at least two of the mood, the physical state, the psychosocial state, and the neurological state of the person,
communicating the nursing assessment report to a medical professional associated with the person.

12. The system as described in claim 11, wherein the nursing-assessment manager is further configured to determine a subsequent psychosocial and neurological state assessment question to ask based on the responses of the person to one or more previously asked psychosocial and neurological state assessment questions.

13. The system as described in claim 11, wherein the interfaces include one or more speakers and one or more microphones, the one or more speakers configured to audibly output the determined psychosocial and neurological state assessment questions, and the one or more speakers configured to capture verbal responses of the person.

14. The system as described in claim 13, wherein the interfaces include a display configured to visually output the determined psychosocial and neurological state assessment questions, the display further configured with touch functionality to capture the responses that are received through touch input.

15. The system as described in claim 14, wherein:
the interfaces are configured to output a message asking whether the person would like a live health care professional to be contacted to follow up with the person; and
responsive to receipt of an indication to contact a live health care professional, the nursing-assessment manager is configured to communicate a request for a live health care professional to follow up with the person.

16. The system as described in claim 11, wherein the nursing-assessment manager is further configured to store the determined mood and physical state in locally stored medical records associated with the person.

17. The system as described in claim 11, wherein the nursing-assessment manager is further configured to communicate data indicative of the determined mood and physical state to a remote computing device for storage as part of medical records associated with the person.

18. A computer-implemented method comprising:
determining, by one or more computing devices, a mood and a physical state, at a first time, of a person, the determination based on video captured of the person in association with the first time;
determining, by the one or more computing devices, a psychosocial state and a neurological states of the person, at the first time, based on an analysis of responses to psychosocial and neurological state assessment questions that are received in association with the first time, the questions determined, at least in part, based on the determined mood and physical state at the first time;
determining, by the one or more computing devices, the mood and physical state, at a second time, of the person, the determination based on additional video captured of the person in association with the second time;
determining, by the one or more computing devices, the psychosocial state and the neurological states of the person, at the second time, based on an analysis of responses to psychosocial and neurological state assessment questions that are received in association with the second time, the questions determined, at least in part, based on the determined mood and physical state at the second time;
determining a health trend for the person based on a comparison made by the one or more computing devices of at least one of the mood, the physical state, the psychosocial state, or the neurological state determined at the first and second times; and
communicating, by the one or more computing devices, the health trend for the person to a medical professional associated with the person.

19. The computer-implemented method as described in claim 18, further comprising determining which of the psychosocial and neurological state assessment questions to output in association with the second time based in part on the responses received in association with the first time.

20. The computer-implemented method as described in claim 18, further comprising, responsive to receiving an indication that the person requests that a live health care professional follow up with the person, including the request as part of the communication to the medical professional.

* * * * *